US010921399B2

(12) United States Patent
Hushek et al.

(10) Patent No.: US 10,921,399 B2
(45) Date of Patent: Feb. 16, 2021

(54) RADIO FREQUENCY (RF) COIL ARRAY FOR A MAGNETIC RESONANCE IMAGING (MRI) SYSTEM FOR USE IN INTERVENTIONAL AND SURGICAL PROCEDURES

(71) Applicant: GE Precision Healthcare LLC, Wauwatosa, WI (US)

(72) Inventors: Stephen Gerard Hushek, Milwaukee, WI (US); Scott Allen Lindsay, Dousman, WI (US); Robert Steven Stormont, Hartland, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 16/194,597

(22) Filed: Nov. 19, 2018

(65) Prior Publication Data

US 2019/0154774 A1    May 23, 2019

Related U.S. Application Data

(60) Provisional application No. 62/590,036, filed on Nov. 22, 2017.

(51) Int. Cl.
*G01R 33/3415* (2006.01)
*A61B 5/055* (2006.01)
(Continued)

(52) U.S. Cl.
CPC ......... *G01R 33/3415* (2013.01); *A61B 5/055* (2013.01); *G01R 33/34007* (2013.01);
(Continued)

(58) Field of Classification Search
CPC .......... G01R 33/3415; G01R 33/34007; G01R 33/34046; G01R 33/365; G01R 33/3657;
(Continued)

(56) References Cited

U.S. PATENT DOCUMENTS

| 4,594,566 | A | * | 6/1986 | Maudsley | ........ G01R 33/34046 |
| | | | | | 324/307 |
| 4,621,237 | A | * | 11/1986 | Timms | ................. G01R 33/341 |
| | | | | | 324/318 |

(Continued)

FOREIGN PATENT DOCUMENTS

| CN | 109521381 A | * | 3/2019 | ....... G01R 33/34007 |
| CN | 109814054 A | * | 5/2019 | ......... G01R 33/3685 |

(Continued)

OTHER PUBLICATIONS

Lechene et al; High quality printed receive coils for clothing integration, PowerPoint presentation; ISMRM 24th Annual Meeting & Exhibition, May 7-13, 2016; Singapore; 20 pages.

(Continued)

*Primary Examiner* — Dixomara Vargas
*Assistant Examiner* — Sean Curtis
(74) *Attorney, Agent, or Firm* — Armstrong Teasdale LLP

(57) ABSTRACT

Various methods and systems are provided for a flexible, lightweight, low-cost radio frequency (RF) coil array of a magnetic resonance imaging (MRI) system. In one example, a RF coil assembly for a MRI system includes a loop portion comprising distributed capacitance wire conductors, a coupling electronics portion including a pre-amplifier. A coupler slidably connects two adjacent coil loops together. An open area is formed inside the loops enabling tissue manipulation or biopsies from interventional or surgical procedures.

20 Claims, 10 Drawing Sheets

(51) Int. Cl.
*G01R 33/34* (2006.01)
*G01R 33/36* (2006.01)
*G01R 33/28* (2006.01)

(52) U.S. Cl.
CPC ..... *G01R 33/34046* (2013.01); *G01R 33/365* (2013.01); *G01R 33/3657* (2013.01); *G01R 33/3685* (2013.01); *G01R 33/285* (2013.01)

(58) Field of Classification Search
CPC .... G01R 33/3685; G01R 33/285; A61B 5/055
USPC .................................................. 324/300–322
See application file for complete search history.

(56) References Cited

U.S. PATENT DOCUMENTS

| | | | | |
|---|---|---|---|---|
| 4,680,548 A * | 7/1987 | Edelstein | ........... | G01R 33/3628 324/318 |
| 4,775,837 A * | 10/1988 | Roschmann | ......... | G01R 33/341 324/318 |
| 4,825,162 A * | 4/1989 | Roemer | ............. | G01R 33/3415 324/312 |
| 4,835,472 A * | 5/1989 | Zabel | .................... | G01R 33/341 324/318 |
| 4,881,034 A * | 11/1989 | Kaufman | ........... | G01R 33/3415 324/318 |
| 5,081,418 A * | 1/1992 | Hayes | .............. | G01R 33/34046 324/318 |
| 5,435,302 A * | 7/1995 | Lenkinski | .............. | G01R 33/34 324/318 |
| 5,477,146 A * | 12/1995 | Jones | ............... | G01R 33/34046 324/318 |
| 5,548,218 A * | 8/1996 | Lu | .......................... | G01R 33/34 324/318 |
| 5,619,996 A * | 4/1997 | Beresten | .......... | G01R 33/34046 324/318 |
| 5,682,098 A * | 10/1997 | Vij | ..................... | G01R 33/3415 324/318 |
| 5,905,378 A * | 5/1999 | Giaquinto | ........ | G01R 33/34084 324/318 |
| 6,029,082 A * | 2/2000 | Srinivasan | ........ | G01R 33/34046 324/318 |
| 6,084,411 A * | 7/2000 | Giaquinto | ........ | G01R 33/34084 324/318 |
| 6,316,941 B1 * | 11/2001 | Fujita | ............... | G01R 33/34046 324/318 |
| 6,441,615 B1 * | 8/2002 | Fujita | ................... | G01R 33/34 324/318 |
| 6,501,980 B1 * | 12/2002 | Carlon | ............... | A61B 5/055 324/318 |
| 6,522,143 B1 * | 2/2003 | Fujita | ............... | G01R 33/34046 324/318 |
| 6,591,128 B1 * | 7/2003 | Wu | .................. | G01R 33/34084 324/318 |
| 6,636,040 B1 * | 10/2003 | Eydelman | ........ | G01R 33/34053 324/318 |
| 6,650,926 B1 * | 11/2003 | Chan | .................. | G01R 33/3415 324/318 |
| 6,727,698 B1 * | 4/2004 | Eydelman | ........ | G01R 33/34053 324/318 |
| 6,727,701 B1 * | 4/2004 | Jevtic | .................... | G01R 33/341 324/318 |
| 6,747,452 B1 * | 6/2004 | Jectic | ............... | G01R 33/3657 324/311 |
| 6,788,058 B1 * | 9/2004 | Petropoulos | ..... | G01R 33/34046 324/318 |
| 6,836,117 B2 * | 12/2004 | Tamura | ............. | G01R 33/3678 324/318 |
| 6,842,004 B2 * | 1/2005 | Withers | ............... | G01R 33/341 324/318 |
| 6,847,210 B1 * | 1/2005 | Eydelman | ........... | G01R 33/341 324/318 |
| 6,980,000 B2 * | 12/2005 | Wong | ............... | G01R 33/34053 324/318 |
| 7,177,671 B2 * | 2/2007 | Nabetani | ................ | A61B 5/055 600/410 |
| 7,212,002 B2 * | 5/2007 | Greim | .................. | G01R 33/341 324/318 |
| 7,268,554 B2 * | 9/2007 | Vaughan | .......... | G01R 33/34046 324/318 |
| 7,288,938 B2 * | 10/2007 | Chmielewski | ... | G01R 33/34046 324/318 |
| 7,365,542 B1 * | 4/2008 | Rohling | ........... | G01R 33/34084 324/318 |
| 7,450,984 B2 * | 11/2008 | Engelhard | ............ | G01R 33/341 324/318 |
| 7,477,056 B2 * | 1/2009 | Renz | ................. | G01R 33/34046 324/318 |
| 7,619,416 B2 * | 11/2009 | Nordmeyer-Massner | .................... | G01R 33/34046 324/318 |
| 7,635,980 B2 * | 12/2009 | Kato | ...................... | G01R 33/30 324/318 |
| 7,659,719 B2 * | 2/2010 | Vaughan | ............. | G01R 33/3678 324/318 |
| 7,945,308 B2 | 5/2011 | Tropp et al. | | |
| 7,970,452 B2 * | 6/2011 | Piron | ..................... | A61B 8/406 600/411 |
| 7,999,548 B1 * | 8/2011 | Brown | ............... | G01R 33/3678 324/318 |
| 8,046,046 B2 * | 10/2011 | Chan | .................. | G01R 33/3415 600/422 |
| 8,179,136 B2 * | 5/2012 | Chan | .................... | G01R 33/365 324/318 |
| 8,207,736 B2 * | 6/2012 | Chu | ................... | G01R 33/3657 324/322 |
| 8,269,498 B2 * | 9/2012 | Zhang | ............... | G01R 33/3415 324/318 |
| 8,362,776 B2 * | 1/2013 | Chu | ................... | G01R 33/3415 324/318 |
| 8,441,258 B2 * | 5/2013 | Chan | ................. | G01R 33/3415 324/318 |
| 8,487,620 B2 * | 7/2013 | Brown | ................. | A61B 5/0555 324/318 |
| 8,560,051 B2 * | 10/2013 | Piron | ..................... | A61B 90/11 600/411 |
| 8,598,880 B2 * | 12/2013 | Dalveren | ......... | G01R 33/34084 324/318 |
| 8,624,597 B2 * | 1/2014 | Banerjee | ............ | G01R 33/3415 324/318 |
| 8,896,309 B2 * | 11/2014 | Hahn | .................. | A61B 5/0555 324/318 |
| 9,000,766 B2 * | 4/2015 | Chu | ................. | G01R 33/34084 324/318 |
| 9,002,431 B2 * | 4/2015 | Jones | ............... | G01R 33/34007 600/421 |
| 9,157,971 B2 * | 10/2015 | Shah | ............... | G01R 33/34076 |
| 9,316,709 B2 * | 4/2016 | Hetherington | ..... | G01R 33/3635 |
| 9,519,037 B2 * | 12/2016 | Felmlee | ............ | G01R 33/341 |
| 9,538,991 B2 * | 1/2017 | Menon | ............... | A61B 5/0555 |
| 9,606,203 B2 * | 3/2017 | Ryu | .................. | G01R 33/341 |
| 9,632,152 B2 * | 4/2017 | Lee | ............... | G01R 33/3415 |
| 9,891,299 B1 * | 2/2018 | Stormont | ........... | G01R 33/3873 |
| 10,132,883 B2 * | 11/2018 | Chu | .................... | G01R 33/365 |
| 10,168,401 B2 * | 1/2019 | Hou | ............... | G01R 33/34007 |
| 10,184,999 B2 * | 1/2019 | Jeong | ............... | G01R 33/34007 |
| 10,219,723 B2 * | 3/2019 | Menon | ................. | G01R 33/285 |
| 10,520,563 B2 * | 12/2019 | Gruber | ...................... | H01F 6/06 |
| 10,524,690 B2 * | 1/2020 | Rapoport | ............ | A61G 11/00 |
| 10,684,333 B2 * | 6/2020 | Hou | ............... | G01R 33/34007 |
| 2002/0180442 A1 * | 12/2002 | Vij | ..................... | G01R 33/3415 324/322 |
| 2003/0050557 A1 * | 3/2003 | Susil | .................. | A61B 18/1492 600/424 |
| 2003/0146750 A1 * | 8/2003 | Vaughan, Jr. | .... | G01R 33/34046 324/318 |
| 2004/0032262 A1 * | 2/2004 | Withers | ............... | G01R 33/341 324/318 |

(56) References Cited

U.S. PATENT DOCUMENTS

| | | | |
|---|---|---|---|
| 2004/0100260 A1* | 5/2004 | Jevtic | G01R 33/3657 324/311 |
| 2004/0220469 A1* | 11/2004 | Jevtic | G01R 33/4828 600/422 |
| 2005/0007116 A1* | 1/2005 | Davis | G01R 33/365 324/318 |
| 2007/0016003 A1* | 1/2007 | Piron | A61B 90/11 600/415 |
| 2007/0040555 A1* | 2/2007 | Wohlfarth | G01R 33/3415 324/318 |
| 2007/0090840 A1* | 4/2007 | Chmielewski | G01R 33/34046 324/318 |
| 2008/0024133 A1* | 1/2008 | Vaughan | G01R 33/3453 324/318 |
| 2008/0204021 A1* | 8/2008 | Leussler | G01R 33/3415 324/318 |
| 2008/0246478 A1* | 10/2008 | Kato | G01R 33/341 324/318 |
| 2008/0284435 A1* | 11/2008 | Overweg | G01R 33/341 324/318 |
| 2010/0033177 A1* | 2/2010 | Ochi | G01R 33/365 324/307 |
| 2011/0166437 A1* | 7/2011 | Chang | A61B 5/055 600/411 |
| 2012/0086452 A1* | 4/2012 | Dohata | G01R 33/3456 324/318 |
| 2012/0112748 A1* | 5/2012 | Hetherington | G01R 33/3635 324/318 |
| 2012/0126815 A1* | 5/2012 | Hahn | A61B 5/0555 324/318 |
| 2012/0161769 A1* | 6/2012 | Banerjee | G01R 33/3415 324/318 |
| 2012/0172704 A1* | 7/2012 | Piron | A61B 5/415 600/410 |
| 2013/0093425 A1* | 4/2013 | Chu | G01R 33/365 324/318 |
| 2013/0119991 A1* | 5/2013 | Soutome | A61B 5/055 324/322 |
| 2013/0317346 A1* | 11/2013 | Alagappan | A61B 5/0555 600/415 |
| 2013/0320981 A1* | 12/2013 | Bulumulla | G01R 33/34007 324/318 |
| 2013/0335086 A1* | 12/2013 | Shah | G01R 33/34007 324/322 |
| 2014/0159727 A1* | 6/2014 | Lee | G01R 33/34092 324/322 |
| 2014/0197833 A1* | 7/2014 | Ryu | G01R 33/341 324/309 |
| 2014/0210466 A1* | 7/2014 | Arias | G01R 33/34084 324/309 |
| 2014/0213886 A1* | 7/2014 | Menon | A61B 10/0233 600/411 |
| 2014/0225613 A1* | 8/2014 | Reykowski | G01R 33/36 324/309 |
| 2015/0028873 A1* | 1/2015 | Dohata | G01R 33/3415 324/322 |
| 2015/0173678 A1* | 6/2015 | Jones | G01R 33/34 600/421 |
| 2015/0355297 A1* | 12/2015 | Menon | G01R 33/422 324/322 |
| 2015/0369886 A1* | 12/2015 | Menon | G01R 33/365 324/322 |
| 2016/0022142 A1* | 1/2016 | Bradshaw | G01R 33/34084 600/415 |
| 2016/0089055 A1* | 3/2016 | Rapoport | A61F 7/00 600/415 |
| 2016/0252592 A1* | 9/2016 | Van Den Brink | A61B 5/063 324/307 |
| 2017/0082705 A1* | 3/2017 | Hou | G01R 33/36 |
| 2017/0112410 A1* | 4/2017 | Menon | G01R 33/285 |
| 2017/0168126 A1* | 6/2017 | Jeong | G01R 33/341 |
| 2017/0248666 A1* | 8/2017 | Rothgang | G01R 33/34084 |
| 2017/0343625 A1* | 11/2017 | Chu | H03H 7/40 |
| 2018/0045794 A1* | 2/2018 | Wiggins | G01R 33/34 |
| 2018/0275234 A1* | 9/2018 | Han | A61B 5/4312 |
| 2018/0329005 A1* | 11/2018 | Sodickson | G01R 33/3621 |
| 2018/0348316 A1* | 12/2018 | Du | H01F 27/02 |
| 2019/0056466 A1* | 2/2019 | Chu | G01R 33/3621 |
| 2019/0086489 A1* | 3/2019 | You | G01R 33/34007 |
| 2019/0086490 A1* | 3/2019 | You | G01R 33/3875 |
| 2019/0154773 A1* | 5/2019 | Stack | G01R 33/34084 |
| 2019/0154774 A1* | 5/2019 | Hushek | G01R 33/3657 |
| 2019/0154775 A1* | 5/2019 | Stack | G01R 33/34084 |
| 2019/0154776 A1* | 5/2019 | Hou | G01R 33/34007 |
| 2019/0277926 A1* | 9/2019 | Stormont | G01R 33/54 |
| 2019/0310327 A1* | 10/2019 | Stormont | G01R 33/34007 |
| 2019/0310328 A1* | 10/2019 | Fuqua | G01R 33/3657 |
| 2019/0310329 A1* | 10/2019 | Malik | G01R 33/3621 |
| 2019/0353722 A1* | 11/2019 | Stormont | G01R 33/34007 |
| 2019/0369176 A1* | 12/2019 | Dalveren | G01R 33/34084 |
| 2019/0369180 A1* | 12/2019 | Chang | G01R 33/0005 |
| 2019/0369181 A1* | 12/2019 | Chang | G01R 33/3664 |
| 2019/0369198 A1* | 12/2019 | Chang | G01R 33/283 |
| 2019/0377040 A1* | 12/2019 | Stack | A61B 5/055 |
| 2020/0081080 A1* | 3/2020 | Zemskov | G01R 33/3614 |
| 2020/0158800 A1* | 5/2020 | Taracila | A61G 13/121 |
| 2020/0233048 A1* | 7/2020 | Corea | H05K 1/0242 |
| 2020/0271738 A1* | 8/2020 | Qin | A61B 5/055 |
| 2020/0309876 A1* | 10/2020 | Robb | G01R 33/3415 |
| 2020/0348380 A1* | 11/2020 | Taracila | G01R 33/3415 |

FOREIGN PATENT DOCUMENTS

| | | | | |
|---|---|---|---|---|
| DE | 102006042996 A1 | 10/2007 | | |
| EP | 0366188 A1 * | 5/1990 | | G01R 33/3614 |
| WO | 1984000214 A1 | 1/1984 | | |
| WO | 2010018479 A1 | 2/2010 | | |

OTHER PUBLICATIONS

Bei Zhang et al; High Impedance Detector Arrays for Magnetic Resonance; arXiv: 1709.03416v1 [physics.ins-det]; Sep. 11, 2017; 16 pages.

Corea et al; Screen-printed flexible MRI receive coils; Nature Communications, 7:10839, DOI:10.1038/ncomms10839, www.nature.com/naturecommunications; Mar. 10, 2016; 7 pages.

European Application No. 17874088.2 filed Nov. 22, 2017 , European extended Search Report dated Jun. 26, 2020; 11 pages.

Oppelt et al., "Low Input Impedance MRI Preamplifier Using a Purely Capacitive Feedback Network", Proceedings of the International Society of the International Society for Magnetic Resonance in Medicine, 14th Scientific Meeting and Exhibition; May 6-12, 2006; p. 2026.

Korean Application No. 10-2019-7015577 filed Nov. 22, 2017,. Office Action dated Sep. 9, 2020; 11 pages.

* cited by examiner

RADIO FREQUENCY (RF) COIL ARRAY FOR A MAGNETIC RESONANCE IMAGING (MRI) SYSTEM FOR USE IN INTERVENTIONAL AND SURGICAL PROCEDURES

CROSS REFERENCE

This application claims benefit and priority to U.S. Provisional Application No. 62/590,036 filed on Nov. 22, 2017, the entirety of which is incorporated herein by reference.

BACKGROUND

Embodiments of the subject matter disclosed herein relate to magnetic resonance imaging (MRI), and more particularly, to MRI radio frequency (RF) coil arrays for use in interventional and surgical procedures.

Magnetic resonance imaging (MRI) is a medical imaging modality that can create images of the inside of a human body without using x-rays or other ionizing radiation. MRI systems include a superconducting magnet to create a strong, uniform, static magnetic field. When a human body, or part of a human body, is placed in the magnetic field, the nuclear spins associated with the hydrogen nuclei in tissue water become polarized, wherein the magnetic moments associated with these spins become preferentially aligned along the direction of the magnetic field, resulting in a small net tissue magnetization along that axis. MRI systems also include gradient coils that produce smaller amplitude, spatially-varying magnetic fields with orthogonal axes to spatially encode the magnetic resonance (MR) signal by creating a signature resonance frequency at each location in the body. Radio frequency (RF) coils are then used to create pulses of RF energy at or near the resonance frequency of the hydrogen nuclei, which add energy to the nuclear spin system. As the nuclear spins relax back to their rest energy state, they release the absorbed energy in the form of an MR signal. This signal is detected by the MRI system and is transformed into an image using reconstruction algorithms.

As mentioned, RF coils are used in MRI systems to transmit RF excitation signals ("transmit coil"), and to receive the MR signals emitted by an imaging subject ("receive coil"). Coil-interfacing cables may be used to transmit signals between the RF coils and other aspects of the processing system, for example to control the RF coils and/or to receive information from the RF coils. However, conventional RF coils tend to be bulky, rigid and are configured to be maintained at a fixed position relative to other RF coils in an array. This bulkiness and lack of flexibility often prevents the RF coil loops from coupling most efficiently with the desired anatomy and make them very uncomfortable to the imaging subject. Further, coil-to-coil interactions dictate that the coils be sized and/or positioned non-ideally from a coverage or imaging acceleration perspective.

There is a desire and need to provide low-cost, flexible, and lightweight RF coil arrays for MRI systems for use before, during or after interventional and/or surgical procedures.

BRIEF DESCRIPTION

In one embodiment, an anterior radio frequency (RF) coil array for a magnetic resonance imaging (MRI) system includes a distributed capacitance loop portion comprising two parallel wire conductors encapsulated and separated by a dielectric material, the two parallel wire conductors maintained separate by the dielectric material along an entire length of the loop portion between terminating ends thereof, a coupling electronics portion including a pre-amplifier, and a coil-interfacing cable including a plurality of baluns or common mode traps positioned in a continuous and/or contiguous manner. The loop portion may deform, elongate and/or change its shape and size, which may allow coils to conform to subject anatomy, increase coverage of anatomy by the coils, allow the coils to bend around other devices that may be attached to the subject, such as a skull clamp used during neurosurgery, or enable passage of an interventional device, such as a biopsy needle or ablation device, through the opening in a coil loop. In this way, a flexible RF coil assembly may be provided that allows for RF coils in an array to be positioned more arbitrarily, allowing placement and/or size of the coils to be based on desired anatomy coverage, without having to account for fixed coil overlaps or electronics positioning. Additionally, the cost and weight of the coils may be significantly reduced due to minimized materials and production process, and environmentally-friendlier processes may be used in the manufacture and miniaturization of the RF coils of the present disclosure versus conventional coils.

Further, the lack of packaging or other material around or between the RF coils elements (i.e., coil loops, coupling electronics) would allow a clinician to perform an interventional or surgical procedure through the opening in the coil loops. Additionally, the coil configuration can be changed, allowing the clinician to change the coil shape from a circle to an ellipse, square, rectangle or some other shape, whichever is optimum for a particular interventional or surgical procedure.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
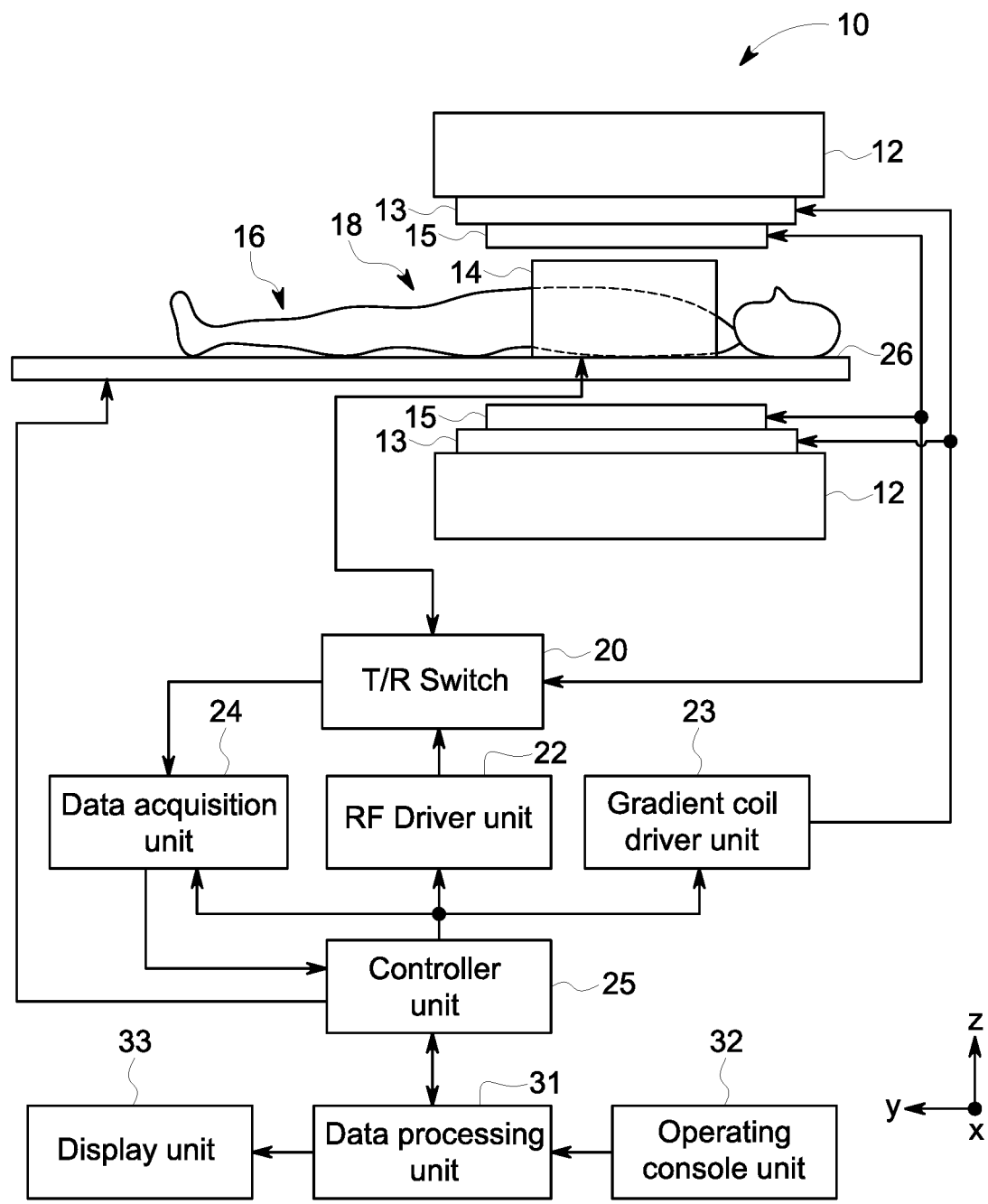
FIG. 1 is a block diagram of an MRI system in accordance with an exemplary embodiment.

The following description relates to various embodiments of a radio frequency (RF) coil in MRI systems. In particular, systems and methods are provided for a low-cost, flexible, and lightweight RF coil that is effectively transparent in multiple respects. The RF coil is effectively transparent to subjects, given the low weight of the coil and flexible packaging that is enabled by the RF coil. The RF coil is also effectively transparent to other RF coils in an array of RF coils, due to minimization of magnetic and electric coupling effects. Further, the RF coil is effectively transparent to other structures through capacitance minimization and is transparent to positrons through mass reduction, enabling use of the RF coil in hybrid positron emission tomography (PET)/MR imaging systems. The RF coil of the present disclosure may be used in MRI systems of various magnetic field strengths.

The RF coil of the present disclosure includes a significantly smaller amount of copper, printed circuit board (PCB) material and electronic components than what is used in a conventional RF coil. The RF coil disclosed herein includes parallel elongated wire conductors, encapsulated and separated by a dielectric material, forming the coil element. The parallel wire conductors form a low reactance structure without need for discrete capacitors. The minimal conductor, sized to keep losses tolerable, eliminates much of the capacitance between coil loops, and reduces electric field coupling. By interfacing with a large sampling impedance, currents are reduced and magnetic field coupling is minimized. The electronics are minimized in size and content to keep mass and weight low and prevent excessive interaction with the desired fields. Packaging around the RF coils elements (i.e., coil loops, coupling electronics) is minimized or eliminated, thus allowing contouring to anatomy, optimizing signal to noise ratio (SNR), imaging acceleration and tissue access, enabling tissue manipulation from interventional or surgical procedures without having to remove the RF coil array.

A traditional receive coil for MR is comprised of several conductive intervals joined between themselves by capacitors. By adjusting the capacitors' capacitances, the impedance of the RF coil may be brought to its minimal value, usually characterized by low resistance. At resonant frequency, stored magnetic and electric energy alternate periodically. Each conductive interval, due to its length and width, possesses a certain self-capacitance, where electric energy is periodically stored as static electricity. The distribution of this electricity takes place over the entire conductive interval length of the order of 5-15 cm, causing similar range electric dipole field. In a proximity of a large dielectric load, self-capacitance of the intervals change—hence detuning the coil. In case of a lossy dielectric, dipole electric field causes Joule dissipation characterized by an increase overall resistance observed by the coil.

In contrast, the RF coil of the present disclosure represents almost an ideal magnetic dipole antenna as its common mode current is uniform in phase and amplitude along its perimeter. The capacitance of the RF coil is built between the two wire conductors along the perimeter of the loop. The conservative electric field is strictly confined within the small cross-section of the two parallel wires and dielectric filler material. In the case of two RF coils overlapping, the parasitic capacitance at the cross-overs or overlaps is greatly reduced in comparison to two overlapped copper traces. RF coil thin cross-sections allows better magnetic decoupling and reduces or eliminates critical overlap between two loops in comparison to two traditional trace-based loops.

FIG. 1 illustrates a magnetic resonance imaging (MRI) apparatus 10 that includes a superconducting magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a table 26, a data processing unit 31, an operating console unit 32, and a display unit 33. In one example, the RF coil unit 14 is a surface coil, which is a local coil that is typically placed proximate to the anatomy of interest of a subject 16. Herein, the RF body coil unit 15 is a transmit coil that transmits RF signals, and the local surface RF coil unit 14 receives MR signals. As such, the transmit body coil (e.g., RF body coil unit 15) and the surface receive coil (e.g., RF coil unit 14) are independent but electromagnetically coupled structures. The MRI apparatus 10 transmits electromagnetic pulse signals to the subject 16 placed in an imaging space 18 with a static magnetic field formed to perform a scan for obtaining MR signals from the subject 16 to reconstruct an image of the subject 16 based on the MR signals obtained by the scan.

The superconducting magnet unit 12 includes, for example, an annular superconducting magnet, which is mounted within a toroidal vacuum vessel. The magnet defines a cylindrical space surrounding the subject 16, and generates a constant, strong, uniform, static magnetic field along the Z direction of the cylindrical space.

The MRI apparatus 10 also includes the gradient coil unit 13 that generates a gradient magnetic field in the imaging space 18 so as to provide the MR signals received by the RF coil unit 14 with three-dimensional positional information. The gradient coil unit 13 includes three gradient coil systems, each of which generates a gradient magnetic field, which inclines into one of three spatial axes perpendicular to each other, and generates a gradient magnetic field in each of a frequency encoding direction, a phase encoding direction, and a slice selection direction in accordance with the imaging condition. More specifically, the gradient coil unit 13 applies a gradient magnetic field in the slice selection direction of the subject 16, to select the slice; and the RF body coil unit 15 transmits an RF signal to a selected region of interest (ROI) of the subject 16 and excites it. The gradient coil unit 13 also applies a gradient magnetic field in the phase encoding direction of the subject 16 to phase encode the MR signals from the ROI excited by the RF signal. The gradient coil unit 13 then applies a gradient magnetic field in the frequency encoding direction of the subject 16 to frequency encode the MR signals from the ROI excited by the RF signal.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field is formed by the superconducting magnet unit 12, the RF coil unit 15 transmits, based on a control signal from the controller unit 25, an RF pulse that is an electromagnet wave to the subject 16 and thereby generates a high-frequency magnetic field. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field produced by the superconducting magnet unit 12 within the imaging space 18 to excite the nuclei. In contrast to the RF coil unit 14, which may be disconnected from the MRI apparatus 10 and replaced with another RF coil unit, the RF body coil unit 15 is fixedly attached and connected to the MRI apparatus 10. Furthermore, whereas local coils such as those comprising the RF coil unit 14 can transmit to or receive signals from only a localized region of the subject 16, the RF body coil unit 15 generally have a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode, a receive-only mode, or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coil unit 15 and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to predetermined scanning. The recording medium may comprise, for example, a ROM, flexible disk, hard disk, optical disk, magneto-optical disk, CD-ROM, or non-volatile memory. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a touchscreen, keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a two-dimensional (2D) slice image or three-dimensional (3D) image of the subject 16 generated by the data processing unit 31.

During a scan, RF coil array interfacing cables (not shown) may be used to transmit signals between the RF coils (e.g., RF coil unit 14 and RF body coil unit 15) and other aspects of the processing system (e.g., data acquisition unit 24, controller unit 25, and so on), for example to control the RF coils and/or to receive information from the RF coils. As explained previously, the RF body coil unit 15 is a transmit coil that transmits RF signals, and the local surface RF coil unit 14 receives the MR signals. More generally, RF coils are used to transmit RF excitation signals ("transmit coil"), and to receive the MR signals emitted by an imaging subject ("receive coil"). In an example, the transmit and receive coils are a single mechanical and electrical structure or array of structures, with transmit/receive mode switchable by auxiliary circuitry. In other examples, the transmit body coil (e.g., RF body coil unit 15) and the surface receive coil (e.g., RF coil unit 14) may be independent structures that are physically coupled to each other via a data acquisition unit or other processing unit. For enhanced image quality, however, it may be desirable to provide a receive coil that is mechanically and electrically isolated from the transmit coil. In such case it is desirable that the receive coil, in its receive mode, be electromagnetically coupled to and resonant with an RF "echo" that is stimulated by the transmit coil. However, during transmit mode, it may be desirable that the receive coil is electromagnetically decoupled from and therefore not resonant with the transmit coil, during actual transmission of the RF signal. Such decoupling averts a potential problem of noise produced within the auxiliary circuitry when the receive coil couples to the full power of the RF signal. Additional details regarding the uncoupling of the receive RF coil will be described below.

As mentioned previously, traditional RF coils may include acid etched copper traces (loops) on PCBs with lumped electronic components (e.g., capacitors, inductors, baluns, resisters, etc.), matching circuitry, decoupling circuitry, and pre-amplifiers. Such a configuration is typically very bulky, heavy and rigid, and requires relatively strict placement of the coils relative to each other in an array to prevent coupling interactions among coil elements that may degrade image quality. As such, traditional RF coils and RF coil arrays lack flexibility and hence may not conform to a subject's anatomy, degrading imaging quality and comfort. Traditional RF coils are also typically enclosed in rigid housings without apertures or openings, which prevents access to a subject's tissue and prevents tissue manipulation, biopsies, or interventional procedures.

Thus, according to embodiments disclosed herein, an RF coil array, such as RF coil unit 14, may include distributed capacitance wires rather than copper traces on PCBs with lumped electronic components, and may have areas where the RF coil loops and associated coupling electronics are exposed with no packaging around them. As a result, the RF coil array may be lightweight and flexible, allowing the coil loops to be placed directly on a subject's skin and allowing interventional procedures to be performed through the openings in the coil loops. The coupling electronics portion coupling the loop portion of the RF coil (e.g., the distributed capacitance wires) may be miniaturized and utilize a low input impedance pre-amplifier, which is optimized for high source impedance (e.g., due to impedance matching circuitry) and allows flexible overlaps among coil elements in an RF coil array. Further, the RF coil array interfacing cable between the RF coil array and system processing components may be flexible and include integrated transparency functionality in the form of distributed baluns, which avoids rigid electronic components and aids in spreading of the heat load.

Figure 2:
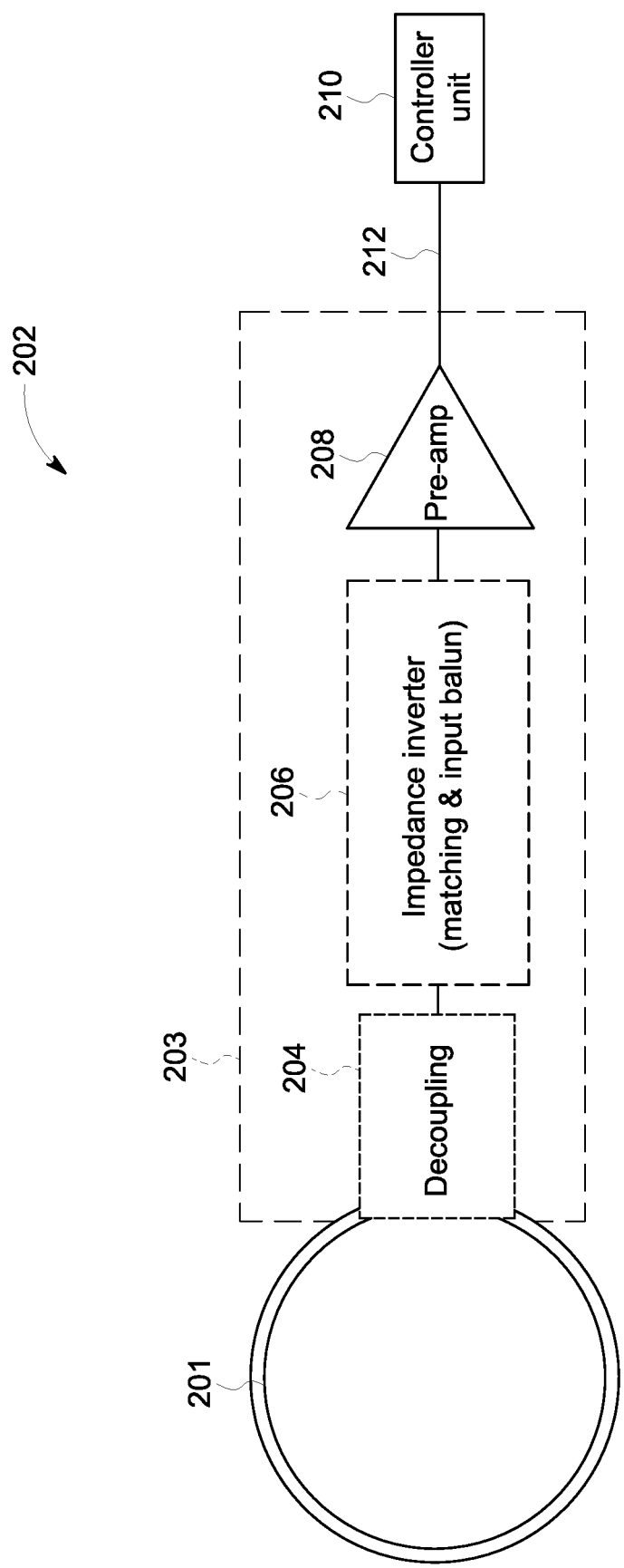
FIG. 2 schematically shows an example RF coil coupled to a controller unit.

Turning now to FIG. 2, a schematic view of an RF coil 202 including a loop portion 201 coupled to a controller unit 210 via a coupling electronics portion 203 and a coil-interfacing cable 212 is shown. In one example, the RF coil may be a surface receive coil, which may be single- or multi-channel. The RF coil 202 is one non-limiting example of RF coil unit 14 of FIG. 1 and as such may operate at one or more frequencies in the MRI apparatus 10. The coil-interfacing cable 212 may be a coil-interfacing cable extending between the electronics portion 203 and an interfacing connector of an RF coil array or a RF coil array interfacing cable extending between the interfacing connector of the RF coil array and the MRI system controller unit 210. The controller unit 210 may be associated with and/or may be a non-limiting example of the data processing unit 31 or controller unit 25 in FIG. 1.

The coupling electronics portion 203 may be coupled to the loop portion of the RF coil 202. Herein, the coupling electronics portion 203 may include a decoupling circuit 204, impedance inverter circuit 206, and a pre-amplifier 208. The decoupling circuit 204 may effectively decouple the RF coil during a transmit operation. Typically, the RF coil 202 in its receive mode may be coupled to a body of a subject being imaged by the MR apparatus in order to receive echoes of the RF signal transmitted during the transmit mode. If the RF coil 202 is not used for transmission, then it may be necessary to decouple the RF coil 202 from the RF body coil while the RF body coil is transmitting the RF signal. The decoupling of the receive coil from the transmit coil may be achieved using resonance circuits and PIN diodes, microelectromechanical systems (MEMS) switches, or another type of switching circuitry. Herein, the switching circuitry may activate detuning circuits operatively connected to the RF coil 202.

The impedance inverter circuit 206 may form an impedance matching network between the RF coil 202 and the pre-amplifier 208. The impedance inverter circuit 206 is configured to transform a coil impedance of the RF coil 202 into an optimal source impedance for the pre-amplifier 208. The impedance inverter circuit 206 may include an impedance matching network and an input balun. The pre-amplifier 208 receives MR signals from the corresponding RF coil 202 and amplifies the received MR signals. In one example, the pre-amplifier may have a low input impedance that is configured to accommodate a relatively high blocking or source impedance. Additional details regarding the RF coil and associated coupling electronics portion will be explained in more detail below with respect to FIGS. 3 and 4. The coupling electronics portion 203 may be packaged in a very small or miniaturized PCB approximately 2 cm$^2$ in size or smaller. The PCB may be protected with a conformal coating or an encapsulating resin. The conformal coating or an encapsulating resin may provide a watertight package that prevents damage to the coupling electronics from any fluid exposure.

The coil-interfacing cable 212, such as a RF coil array interfacing cable, may be used to transmit signals between the RF coils and other aspects of the processing system, for example to control the RF coils and/or to receive information from the RF coils. The RF coil array interfacing cables may be disposed within the bore or imaging space of the MRI apparatus (such as MRI apparatus 10 of FIG. 1) and subjected to electro-magnetic fields produced and used by the MRI apparatus. In MRI systems, coil-interfacing cables, such as coil-interfacing cable 212, may support transmitter-driven common-mode currents, which may in turn create field distortions and/or unpredictable heating of components. Typically, common-mode currents are blocked by using baluns. Baluns or common-mode traps provide high common-mode impedances, which in turn reduces the effect of transmitter-driven currents.

Thus, coil-interfacing cable 212 may include one or more baluns. In traditional coil-interfacing cables, baluns are positioned with a relatively high density, as high dissipation/voltages may develop if the balun density is too low or if baluns are positioned at an inappropriate location. However, this dense placement may adversely affect flexibility, cost, and performance. As such, the one or more baluns in the coil-interfacing cable may be continuous baluns to ensure no high currents or standing waves, independent of positioning. The continuous baluns may be distributed, flutter, and/or butterfly baluns. Additional details regarding the coil-interfacing cable and baluns will be presented below with respect to FIGS. 11, 12 and 13.

Figure 3:
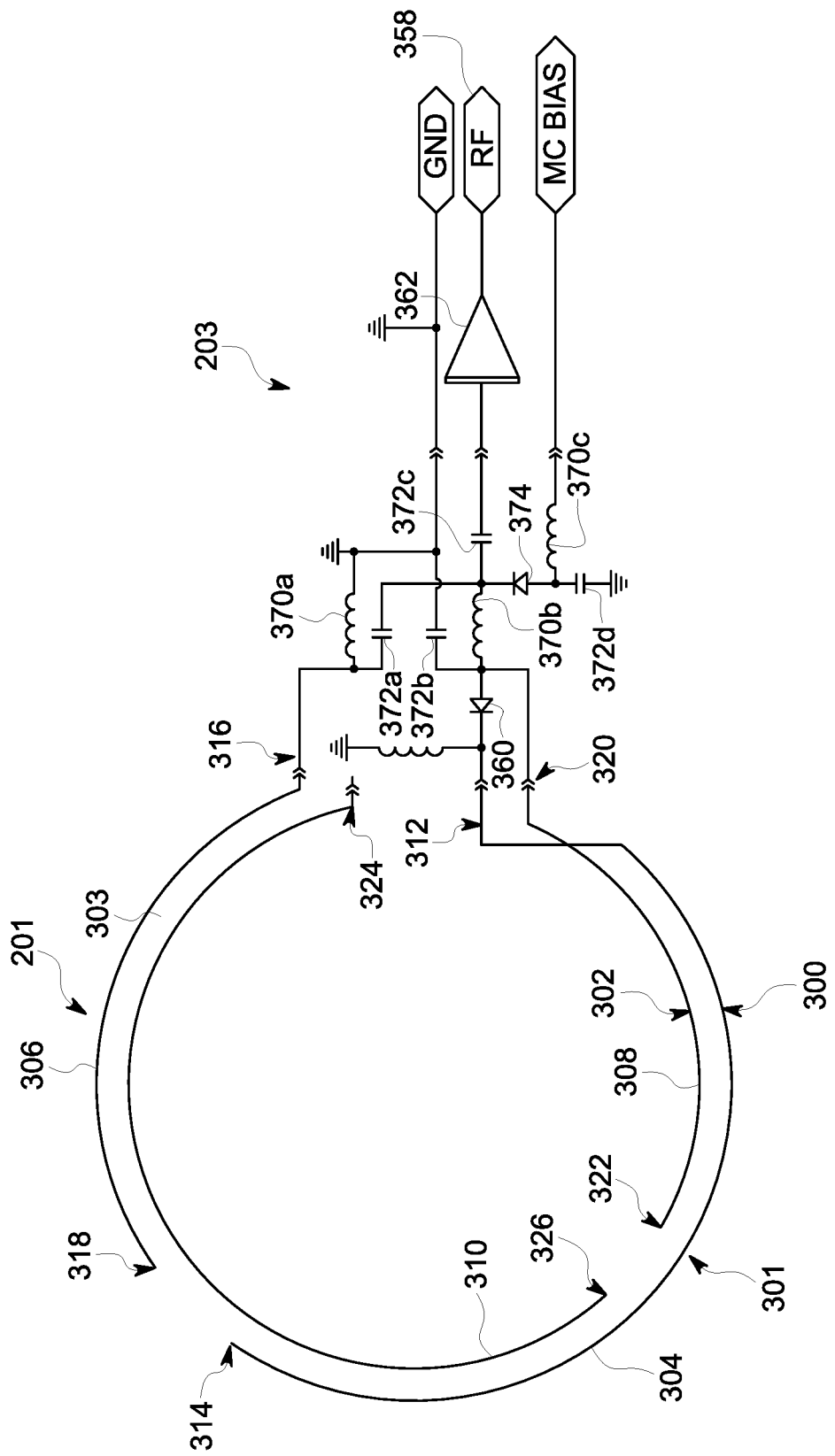
FIG. 3 shows a first example RF coil and associated coupling electronics.

FIG. 3 is a schematic of an RF coil 301 having segmented conductors formed in accordance with an embodiment. RF coil 301 is a non-limiting example of RF coil 202 of FIG. 2 and as such includes loop portion 201 and coupling electronics portion 203 of RF coil 202. The coupling electronics portion allows the RF coil to transmit and/or receive RF signals when driven by the data acquisition unit 124 (shown in FIG. 1). In the illustrated embodiment, the RF coil 301 includes a first conductor 300 and a second conductor 302. The first and second conductors 300, 302 may be segmented such that the conductors form an open circuit (e.g., form a monopole). The segments of the conductors 300, 302 may have different lengths, as is discussed below. The length of the first and second conductors 300, 302 may be varied to achieve a desired distributed capacitance, and accordingly, a desired resonance frequency.

The first conductor 300 includes a first segment 304 and a second segment 306. The first segment 304 includes a driven end 312 at an interface terminating to coupling electronics portion 203, which will be described in more detail below. The first segment 304 also includes a floating end 314 that is detached from a reference ground, thereby maintaining a floating state. The second segment 306 includes a driven end 316 at the interface terminating to the coupling electronics portion and a floating end 318 that is detached from a reference ground.

The second conductor 302 includes a first segment 308 and a second segment 310. The first segment 308 includes a driven end 320 at the interface. The first segment 308 also includes a floating end 322 that is detached from a reference ground, thereby maintaining a floating state. The second segment 310 includes a driven end 324 at the interface, and a floating end 326 that is detached from a reference ground. The driven end 324 may terminate at the interface such that end 324 is only coupled to the first conductor through the distributed capacitance. The capacitors shown around the loop between the conductors represent the capacitance between the wire conductors.

The first conductor 300 and the second conductor 302 exhibit a distributed capacitance along the length of the first and second segments 304, 306, 308, 310. The first segments 304, 308 may have a different length than the second segments 306, 310. The relative difference in length between the first segments 304, 308 and the second segments 306, 310 may be used to produce an effective LC circuit have a resonance frequency at the desired center frequency. For example, by varying the length of the first segments 304, 308 relative to the lengths of the second segments 306, 310, an integrated distributed capacitance may be varied.

In the illustrated embodiment, the first and second wire conductors 300, 302 are shaped into a loop portion that terminates to an interface. But in other embodiments, other shapes are possible. For example, the loop portion may be a polygon, shaped to conform the contours of a surface (e.g., housing), and/or the like. The loop portion defines a conductive pathway along the first and second conductors. The first and second conductors are void of any discrete or lumped capacitive or inductive elements along an entire length of the conductive pathway. The loop portion may also include loops of varying gauge of stranded or solid conductor wire, loops of varying diameters with varying lengths of the first and second conductors 300, 302, and/or loops of varying spacing between the first and second conductors. For example, each of the first and second conductors may have no cuts or gaps (no segmented conductors) or one or more cuts or gaps (segmented conductors) at various locations along the conductive pathway.

Distributed capacitance (DCAP), as used herein, represents a capacitance exhibited between conductors along the length of the conductors and is void of discrete or lumped capacitive components and discrete or lumped inductive components. In the examples herein, the capacitance may grow in an even and uniform manner along the length of the first and second conductors 300, 302.

A dielectric material 303 encapsulates and separates the first and second conductors 300, 302. The dielectric material 303 may be selectively chosen to achieve a desired distributive capacitance. The dielectric material 303 may be based on a desired permittivity E to vary the effective capacitance of the loop portion. For example, the dielectric material 303 may be air, rubber, plastic, or any other dielectric material. In one example, the dielectric material may be polytetrafluoroethylene (pTFE). For example, the dielectric material 303 may be an insulating material surrounding the parallel conductive elements of the first and second conductors 300, 302. Alternatively, the first and second conductors 300, 302 may be twisted upon one another to form a twisted pair cable. As another example, the dielectric material 303 may be a plastic material. The first and second conductors 300, 302 may form a coaxial structure in which the plastic dielectric material 303 separates the first and second conductors. As another example, the first and second conductors may be configured as planar strips.

The coupling electronics portion 203 is operably and communicatively coupled to the RF driver unit 22, the data acquisition unit 24, controller unit 25, and/or data processing unit 31 to allow the RF coil 102 to transmit and/or receive RF signals. In the illustrated embodiment, the coupling electronics portion 203 includes a signal interface 358 configured to transmit and receive the RF signals. The signal interface 358 may transmit and receive the RF signals via a cable. The cable may be a 3-conductor triaxial cable having a center conductor, an inner shield, and an outer shield. The center conductor is connected to the RF signal and pre-amp control (RF), the inner shield is connected to ground (GND), and the outer shield is connected to the multi-control bias (diode decoupling control) (MC_BIAS). A 10V power connection may be carried on the same conductor as the RF signal.

As explained above with respect to FIG. 2, the coupling electronics portion 203 includes a decoupling circuit, impedance inverter circuit, and pre-amplifier. As illustrated in FIG. 3, the decoupling circuit includes a decoupling diode 360.

The decoupling diode 360 may be provided with voltage from MC_BIAS, for example, in order to turn decoupling diode 360 on. When on, decoupling diode 360 causes conductor 300 to short with conductor 302, thus causing the coil be off-resonance and hence decouple the coil during a transmit operation, for example.

It should be understood that the decoupling circuit shown in FIG. 3 is for illustration not for limitation. Any appropriate decoupling configuration can be used to decouple the RF coil during the transmit operation.

The impedance inverter circuit includes a plurality of inductors, including first inductor 370a, second inductor 370b, and third inductor 370c; a plurality of capacitors, including first capacitor 372a, a second capacitor 372b, a third capacitor 372c, and a fourth capacitor 372d; and a diode 374. The impedance inverter circuit includes matching circuitry and an input balun. As shown, the input balun is a lattice balun that comprises first inductor 370a, second inductor 370b, first capacitor 372a, and second capacitor 372b. In one example, diode 374 limits the direction of current flow to block RF receive signals from proceeding into decoupling bias branch (MC_BIAS).

The pre-amplifier 362 may be a low input impedance pre-amplifier that is optimized for high source impedance by the impedance matching circuitry. The pre-amplifier may have a low noise reflection coefficient, γ, and a low noise resistance, Rn. In one example, the pre-amplifier may have a source reflection coefficient of γ substantially equal to 0.0 and a normalized noise resistance of Rn substantially equal to 0.0 in addition to the low noise figure. However, γ values substantially equal to or less than 0.1 and Rn values substantially equal to or less than 0.2 are also contemplated. With the pre-amplifier having the appropriate γ and Rn values, the pre-amplifier provides a blocking impedance for RF coil 301 while also providing a large noise circle in the context of a Smith Chart. As such, current in RF coil 301 is minimized, the pre-amplifier is effectively noise matched with RF coil 301 output impedance. Having a large noise circle, the pre-amplifier yields an effective SNR over a variety of RF coil impedances while producing a high blocking impedance to RF coil 301.

In some examples, the pre-amplifier 362 may include an impedance transformer that includes a capacitor and an inductor. The impedance transformer may be configured to alter the impedance of the pre-amplifier to effectively cancel out a reactance of the pre-amplifier, such as capacitance caused by a parasitic capacitance effect. Parasitic capacitance effects can be caused by, for example, a PCB layout of the pre-amplifier or by a gate of the pre-amplifier. Further, such reactance can often increase as the frequency increases. Advantageously, however, configuring the impedance transformer of the pre-amplifier to cancel, or at least minimize, reactance maintains a high impedance (i.e. a blocking impedance) to RF coil 301 and an effective SNR without having a substantial impact on the noise figure of the pre-amplifier. The lattice balun described above may be a non-limiting example of an impedance transformer.

In examples, the pre-amplifier described herein may be a low input pre-amplifier. For example, in some embodiments, a "relatively low" input impedance of the preamplifier is less than approximately 5 ohms at resonance frequency. The coil impedance of the RF coil 301 may have any value, which may be dependent on coil loading, coil size, field strength, and/or the like. Examples of the coil impedance of the RF coil 301 include, but are not limited to, between approximately 2 ohms and approximately 10 ohms at 1.5 T magnetic field strength, and/or the like. The impedance inverter circuitry is configured to transform the coil impedance of the RF coil 301 into a relatively high source impedance. For example, in some embodiments, a "relatively high" source impedance is at least approximately 100 ohms and may be greater than 150 ohms.

The impedance transformer may also provide a blocking impedance to the RF coil 301. Transformation of the coil impedance of the RF coil 301 to a relative high source impedance may enable the impedance transformer to provide a higher blocking impedance to the RF coil 301. Exemplary values for such higher blocking impedances include, for example, a blocking impedance of at least 500 ohms, and at least 1000 ohms.

Figure 4:
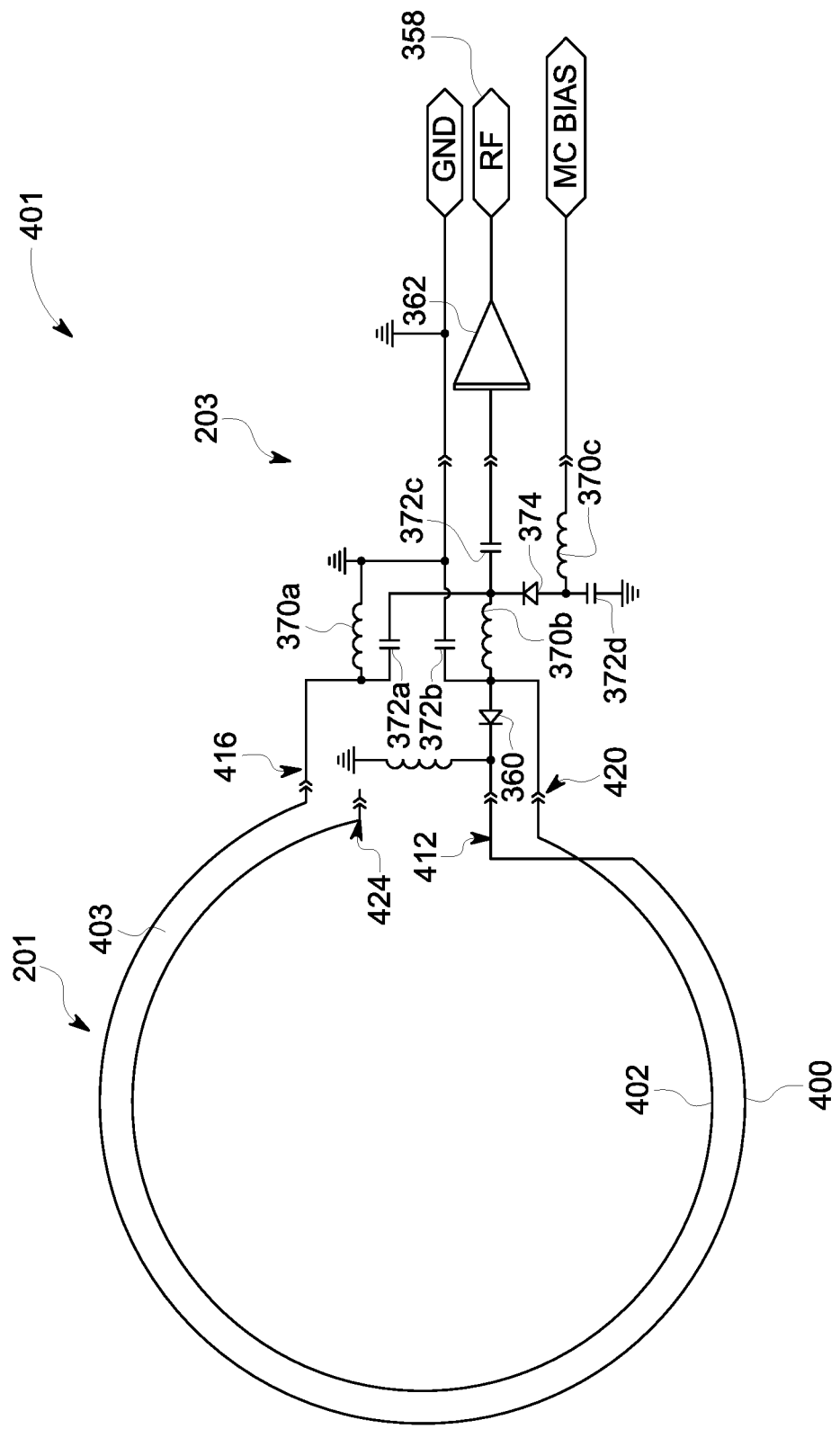
FIG. 4 shows a second example RF coil and associated coupling electronics.

FIG. 4 is a schematic of an RF coil 401 and coupling electronics portion 203 according to another embodiment. The RF coil of FIG. 4 is a non-limiting example of the RF coil and coupling electronics of FIG. 2, and as such includes a loop portion 201 and coupling electronics portion 203. The coupling electronics allows the RF coil to transmit and/or receive RF signals when driven by the data acquisition unit 124 (shown in FIG. 1). The RF coil 401 includes a first conductor 400 in parallel with a second conductor 402. At least one of the first and second conductors 400, 402 are elongated and continuous.

In the illustrated embodiment, the first and second conductors 400, 402 are shaped into a loop portion that terminates to an interface. But in other embodiments, other shapes are possible. For example, the loop portion may be a polygon, shaped to conform the contours of a surface (e.g., housing), and/or the like. The loop portion defines a conductive pathway along the first and second conductors 400, 402. The first and second conductors 400, 402 are void of any discrete or lumped capacitive or inductive components along an entire length of the conductive pathway. The first and second conductors 400, 402 are uninterrupted and continuous along an entire length of the loop portion. The loop portion may also include loops of varying gauge of stranded or solid conductor wire, loops of varying diameters with varying lengths of the first and second conductors 400, 402, and/or loops of varying spacing between the first and second conductors. For example, each of the first and second conductors may have no cuts or gaps (no segmented conductors) or one or more cuts or gaps (segmented conductors) at various locations along the conductive pathway.

The first and second conductors 400, 402 have a distributed capacitance along the length of the loop portion (e.g., along the length of the first and second conductors 400, 402). The first and second conductors 400, 402 exhibit a substantially equal and uniform capacitance along the entire length of the loop portion. Distributed capacitance (DCAP), as used herein, represents a capacitance exhibited between conductors that grows evenly and uniformly along the length of the conductors and is void of discrete or lumped capacitive components and discrete or lumped inductive components. In the examples herein, the capacitance may grow in a uniform manner along the length of the first and second conductors 400, 402. At least one of the first and second conductors 400, 402 are elongated and continuous. In the illustrated embodiment, both the first and second conductors 400, 402 are elongated and continuous. But in other embodiments, only one of the first or second conductors 400, 402 may be elongated and continuous. The first and second conductors 400, 402 form continuous distributed capacitors. The capacitance grows at a substantially constant rate along the length of the conductors 400, 402. In the illustrated embodiment, the first and second conductors 400, 402 form elongated continuous conductors that exhibits DCAP along the length of the first and second conductors 400, 402. The first and second conductors 400, 402 are void of any discrete capacitive and inductive components along the entire length of the continuous conductors between terminating ends of the first and second conductors 400, 402. For example, the first and second conductors 400, 402 do not include any discrete capacitors, nor any inductors along the length of the loop portion.

A dielectric material 403 separates the first and second conductors 400, 402. The dielectric material 403 may be selectively chosen to achieve a select distributive capacitance. The dielectric material 403 may be based on a desired permittivity E to vary the effective capacitance of the loop portion. For example, the dielectric material 403 may be air, rubber, plastic, or any other dielectric material. In one example, the dielectric material may be polytetrafluoroethylene (pTFE). For example, the dielectric material 403 may be an insulating material surrounding the parallel conductive elements of the first and second conductors 400, 402. Alternatively, the first and second conductors 400, 402 may be twisted upon one another to from a twisted pair cable. As another example, the dielectric material 403 may be a plastic material. The first and second conductors 400, 402 may form a coaxial structure in which the plastic dielectric material 403 separates the first and second conductors 400, 402. As another example, the first and second conductors 400, 402 may be configured as planar strips.

The first conductor 400 includes a first terminating end 412 and a second terminating end 416 that terminates at the interface. The first terminating end 412 is coupled to the coupling electronics portion 203. The first terminating end 412 may also be referred to herein as a "drive end." The second terminating end 416 is also referred to herein as a "second drive end."

The second conductor 402 includes a first terminating end 420 and a second terminating end 424 that terminates at the interface. The first terminating end 420 is coupled to the coupling electronics portion 203. The first terminating end 420 may also be referred to herein as a "drive end." The second terminating end 424 is also referred to herein as a "second drive end."

The loop portion 201 of the RF coil 401 is coupled to coupling electronics portion 203. The coupling electronics portion 203 may be the same coupling electronics described above with respect to FIGS. 2 and 3, and hence like reference numbers are given to like components and further description is dispensed with.

As appreciated by FIGS. 3 and 4, the two parallel conductors comprising the loop portion of an RF coil may each be continuous conductors, as illustrated in FIG. 4, or one or both of the conductors may be non-continuous, as illustrated in FIG. 3. For example, both conductors shown in FIG. 3 may include cuts, resulting in each conductor being comprised of two segments. The resulting space between conductor segments may be filled with the dielectric material that encapsulates and surrounds the conductors. The two cuts may be positioned at different locations, e.g., one cut at 135° and the other cut at 225° (relative to where the loop portion interfaces with the coupling electronics). By including discontinuous conductors, the resonance frequency of the coil may be adjusted relative to a coil that includes continuous conductors. In an example, an RF coil that includes two continuous parallel conductors encapsulated and separated by a dielectric, the resonance frequency may be a smaller, first resonance frequency. If that RF coil instead includes one discontinuous conductor (e.g., where one of the conductors is cut and filled with the dielectric material) and one continuous conductor, with all other parameters (e.g., conductor wire gauge, loop diameter, spacing between conductors, dielectric material) being the same, the resonance frequency of the RF coil may be a larger, second resonance frequency. In this way, parameters of the loop portion, including conductor wire gauge, loop diameter, spacing between conductors, dielectric material selection and/or thickness, and conductor segment number and lengths, may be adjusted to tune the RF coil to a desired resonance frequency.

Figure 5:
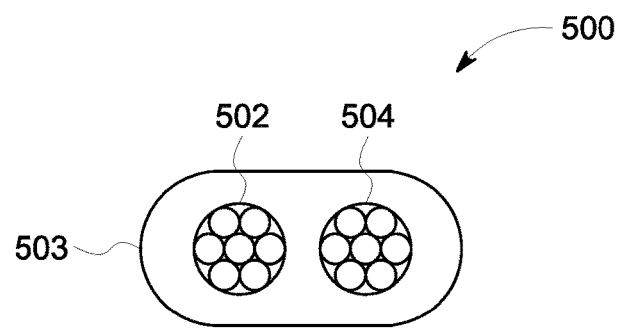
FIG. 5 shows a cross-sectional view of a distributed capacitance loop portion of an example RF coil.

FIG. 5 shows a cross-sectional view of a distributed capacitance loop portion 500 of an example RF coil. As appreciated by FIG. 5, loop portion 500 includes first wire conductor 502 and second wire conductor 504 surrounded by and encapsulated in dielectric material 503. Each wire conductor may have a suitable cross-sectional shape, herein a circular cross-sectional shape. However, other cross-sectional shapes for the wire conductors are possible, such as elliptical, cylindrical, rectangular, triangular, hexagonal, etc. The wire conductors may be separated by a suitable distance, and the distance separating the conductors as well as the diameters of the wire conductors may be selected to achieve a desired capacitance. Further, each of the first wire conductor 502 and second wire conductor 504 may be a seven-conductor stranded wire (e.g., comprised of seven stranded wires), but solid conductors may also be used instead of stranded wire. Stranded wire may provide more flexibility relative to solid conductors, at least in some examples.

Thus, the RF coil described herein includes a twin lead wire conductor loop encapsulated in a dielectric that may have no cuts or at least one cut in at least one of the two parallel wire conductors. The RF coil arrays are adaptable to a broad range of MR operating frequencies by changing the gauge of conductor wire used, spacing between conductor wires, loop diameters, loop shapes, and the number and placement of cuts in the conductor wires.

The conductor wires and coil loops used in the loop portion of the RF coil or RF coil array may be manufactured in any suitable manner to get the desired resonance frequency for a desired RF coil application. The desired conductor wire gauge, such as 28 or 30 American Wire Gauge (AWG) or any other desired wired gauge may be paired with a parallel conductor wire of the same gauge and encapsulated with a dielectric using an extrusion process or a three-dimensional (3D) printing or additive manufacturing process. This manufacturing process may be environmentally friendly with low waste and low-cost.

Figure 6:
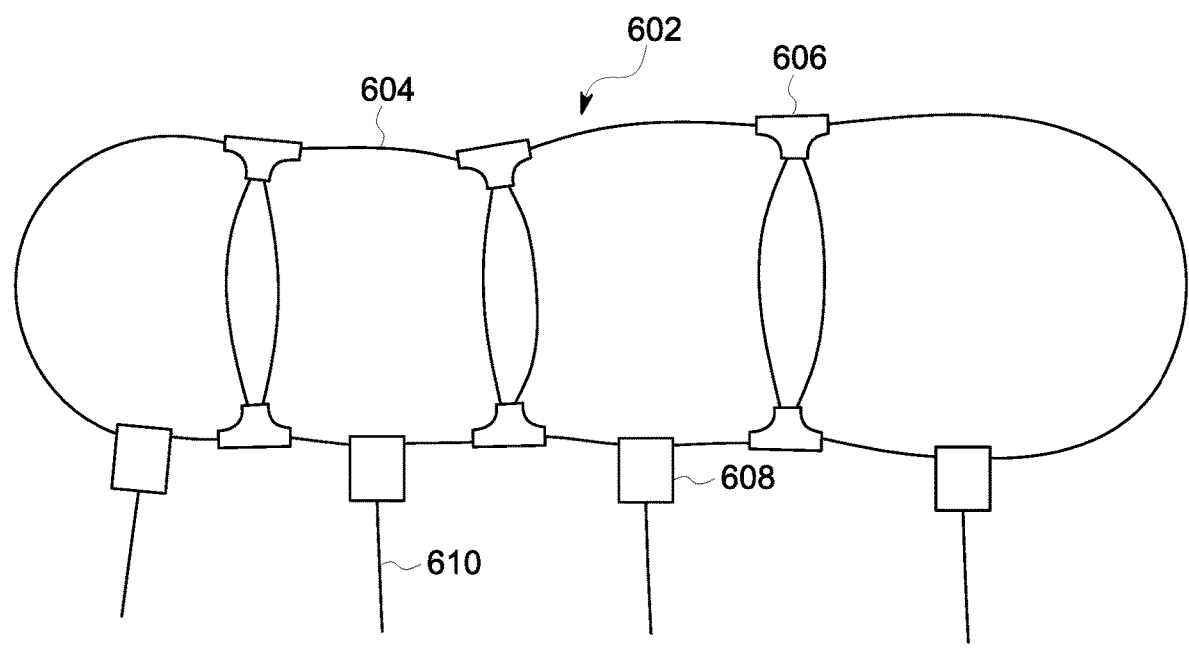
FIG. 6 shows an example RF coil array that may be used with an MRI system in an interventional or surgical procedure.
Figure 8:
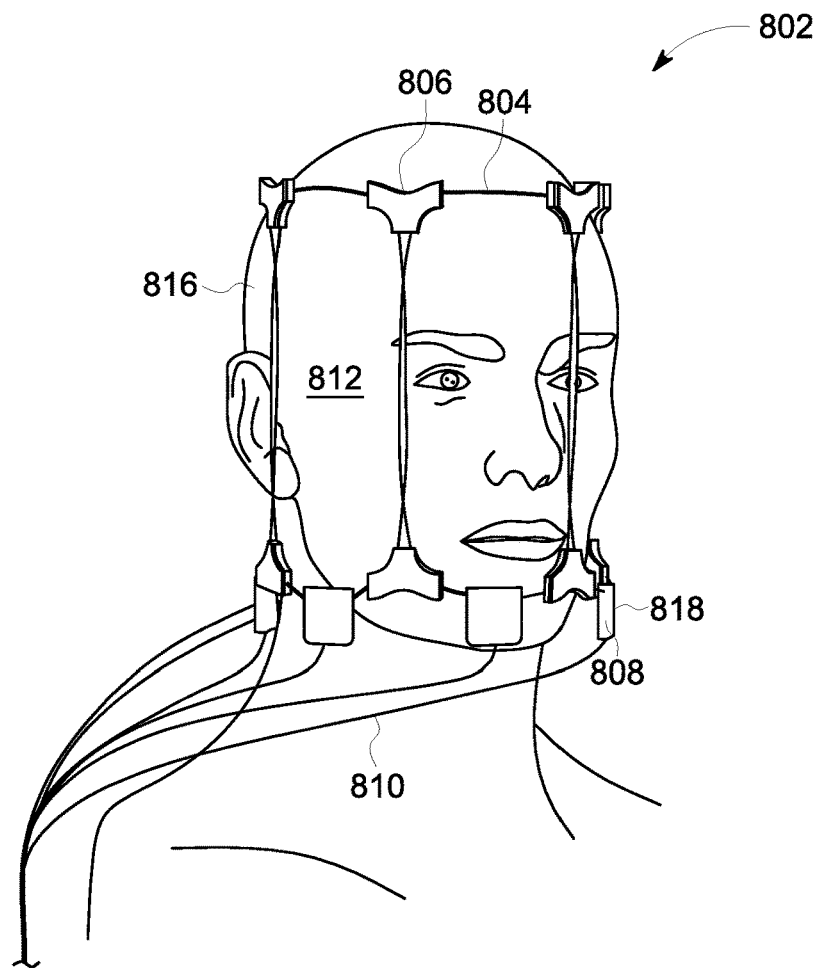
FIG. 8 shows a first example RF coil array placed around the head of a subject undergoing an interventional or surgical procedure.
Figure 9:
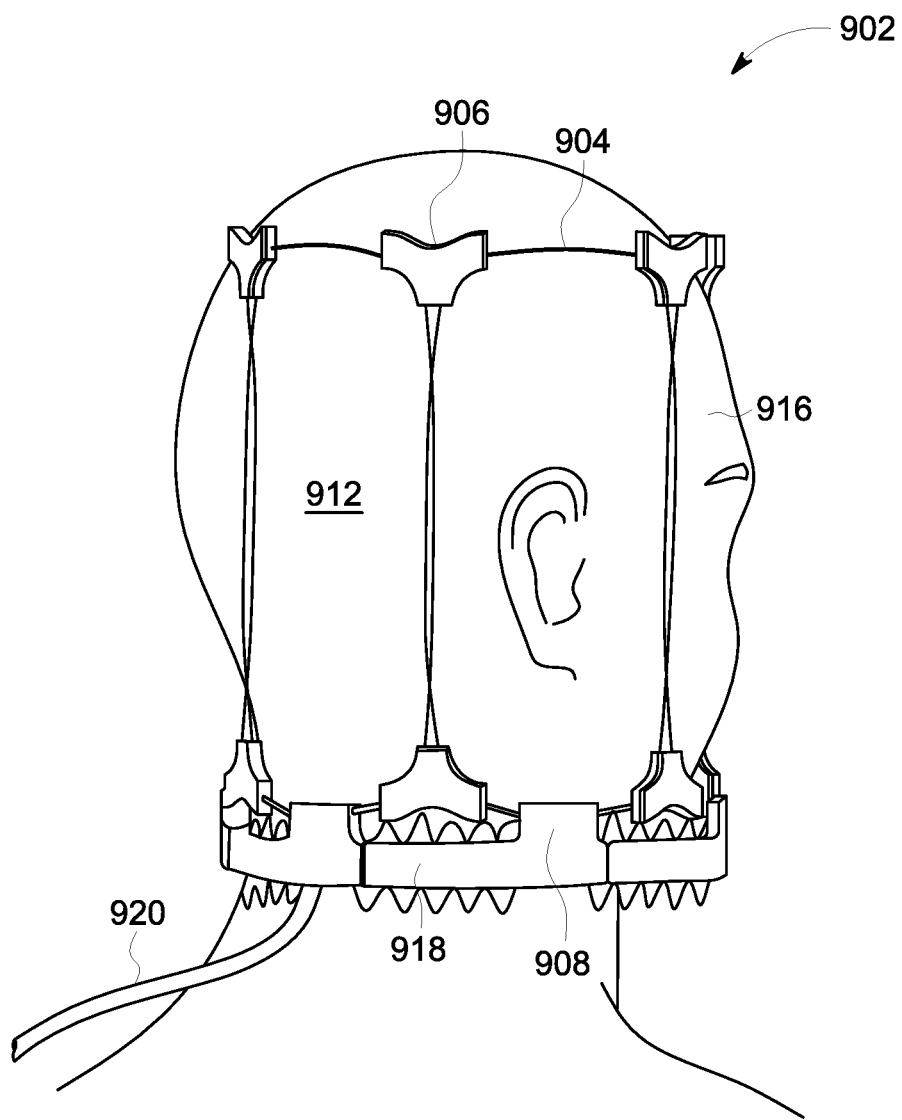
FIG. 9 shows a second example RF coil array placed around the head of a subject undergoing an interventional or surgical procedure.

The RF coils presented above with respect to FIGS. 2-5 may be utilized in order to receive MR signals during an MR imaging session. As such, the RF coils of FIGS. 2-5 may be non-limiting examples of RF coil unit 14 of FIG. 1 and may be configured to be coupled to a downstream component of the MRI system, such as a processing system. The RF coils of FIGS. 2-5 may be present in an array of RF coils having various configurations. FIGS. 6, 8 and 9, described in more detail below, illustrate various embodiments for a RF coil array that may include one or more of the RF coils described above with respect to FIGS. 2-5. The RF coil array may be used with MRI systems for use before, during or after interventional and/or surgical procedures.

FIG. 6 shows an example RF coil array 602 that may be used with an MRI system in an interventional or surgical procedure. The RF coil array 602 comprises a plurality of coil loops 604 with associated miniaturized coupling electronic units 608 or PCBs 608 coupled to each of the coil loops, and a plurality of couplers 606 slidably connecting adjacent coil loops. In the illustrated embodiment, at least two couplers slidably connect two adjacent coil loops. In some examples, the couplers allow the RF coils to be slidably movable relative to each other, such that varying amounts of overlap among coil loops is provided. The couplers 606 are preferable positioned at top and bottom ends or corners of each coil loop, such that there are at least two couplers coupled to the top and bottom ends of RF coils located at outer ends of a RF coil array, and at least four couplers coupled to top and bottom corners of inner adjacent coil loops of a RF coil array.

The coil loops are flexible and may deform from a circular or elliptical shape to a square or rectangular shape. The RF coil loops are encapsulated in dielectric material and the coupling electronics PCBs are encapsulated with a conformal coating or an encapsulating resin. The RF coil loops may be positioned in an overlapping manner. The RF coils array 602 may be attached to a subject's skin with adhesive medical grade tape or adhesive pads.

A coil-interfacing cable 610 extends from each coupling electronics unit 608. The coil interfacing cable 610 may be a 3-conductor triaxial cable having a center conductor, an inner shield, and an outer shield. The center conductor is connected to the RF signal and pre-amp control (RF), the inner shield is connected to ground (GND), and the outer shield is connected to the multi-control bias (diode decoupling control) (MC_BIAS), as described above with reference to FIGS. 3 and 4. A 10V power connection may be carried on the same conductor as the RF signal and pre-amp control (RF). Each coil-interfacing cable may be coupled to at least one balun between each coupling electronics unit and an interface connector. In some examples, the coil-interfacing cables of RF coil array may include continuous and/or contiguous baluns throughout their length to eliminate the cylinder-shaped lumpy baluns.

The RF coil loop elements with miniaturized coupling electronics units may be coated with TEFLON®, a thermoplastic resin, or any suitable material to keep them from getting damaged when exposed to subjects in a medical environment, and because the encapsulating materials are exceptionally durable, the RF coil loop elements and miniaturized coupling electronics units may be autoclaved for cleaning. In some embodiments, the RF coil loop elements with miniaturized coupling electronics units may be disposable.

Figure 7:
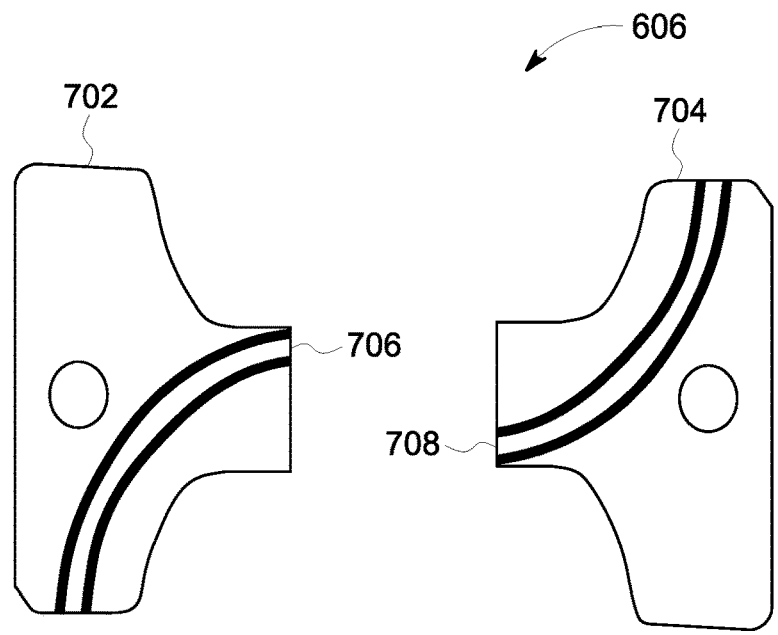
FIG. 7 shows example first and second halves of a coupler for slidable engagement of RF coil loops (loop portion) of the RF coil array.

FIG. 7 shows example first 702 and second 704 halves of a coupler 606 for slidable engagement of RF coil loops (loop portion) of an RF coil array. The first 702 and second 704 halves of the coupler 606 each include a groove 706, 708 formed therein that slidably engages the coil loop. The first 702 and second 704 halves of the coupler 606 removably snap together around the first wire conductor and second wire conductor encapsulated in dielectric material of a coil loop. The coupler may be made of a thermoplastic material or another suitable material.

FIG. 8 shows a first example RF coil array 802 placed around the head 812 of a subject 816 undergoing an interventional or surgical procedure. The RF coil array 802 comprises a plurality of coil loops 804 with associated miniaturized coupling electronic units or PCBs 808 coupled to each of the coil loops, and a plurality of couplers 806 slidably connecting adjacent coil loops. In the illustrated embodiment, at least two couplers slidably connect two adjacent coil loops. In some examples, the couplers allow the RF coils to be slidably movable relative to each other, such that varying amounts of overlap among coil loops is provided.

The coil loops are flexible and may deform, elongate and/or change their shape and size, which may allow the coils to conform to subject anatomy, increase coverage, or bend around interventional or surgical instruments or devices that may be attached to the subject, such as a skull clamp used during neurosurgery, or enable passage of an interventional device, such as a biopsy needle or ablation device, through the opening in a coil loop. For example, the coil loops may deform from a circular or elliptical shape to a square or rectangular shape. In the illustrated embodiment, the RF coil loops are 14 cm in diameter. The RF coil loops are encapsulated in dielectric material and the coupling electronics PCBs may be encapsulated with a conformal coating or an encapsulating resin. The RF coil loops may be positioned in an overlapping manner. In some embodiments, the RF coils array 802 may be attached to a subject's head with adhesive medical grade tape or adhesive pads.

Each of the coupling electronics units 808 is enclosed in a protective housing 818. The protective housing may be made of a thermoplastic material or any suitable material to provide a watertight package that prevents damage to the coupling electronics from any fluid exposure. A coil-interfacing cable 810 extends from each coupling electronics unit 808.

With the RF coil loops not enclosed in a housing, the RF coil array is flexible in multiple dimensions and procedures can be performed through the open areas in the coil loops.

FIG. 9 shows a second example RF coil array 902 placed around the head 912 of a subject 916 undergoing an interventional or surgical procedure. The RF coil array 902 comprises a plurality of coil loops 904 with associated miniaturized coupling electronic units or PCBs 908 coupled to each of the coil loops, and a plurality of couplers 906 slidably connecting adjacent coil loops. In the illustrated embodiment, at least two couplers slidably connect two adjacent coil loops. In some examples, the couplers allow the RF coils to be slidably movable relative to each other, such that varying amounts of overlap among coil loops is provided.

The coil loops are flexible and may deform, elongate and/or change their shape and size, which may allow the coils to conform to subject anatomy, increase coverage, or bend around interventional or surgical instruments or devices that may be attached to the subject, such as a skull clamp used during neurosurgery, or enable passage of an interventional device, such as a biopsy needle or ablation device, through the opening in a coil loop. For example, the coil loops may deform from a circular or elliptical shape to a square or rectangular shape. In the illustrated embodiment, the RF coil loops are 14 cm in diameter. The RF coil loops are encapsulated in dielectric material and the coupling electronics PCBs may be encapsulated with a conformal coating or an encapsulating resin. The RF coil loops may be positioned in an overlapping manner. In some embodiments, the RF coils array 902 may be attached to a subject's head with adhesive medical grade tape or adhesive pads.

Each of the coupling electronics units 908 is enclosed in a protective housing 918. The protective housing may be made of a thermoplastic material or any suitable material to provide a watertight package that prevents damage to the coupling electronics from any fluid exposure. The coupling electronics units 908 may be grouped together and enclosed in the protective housing 918. A coil-interfacing cable (not shown) extends from each coupling electronics unit 908 within the protective housing 918. In the illustrated embodiment, the coil-interfacing cables are bundled together and protected by an accordion style (i.e., foldable) housing 918.

A single grouping of coil-interfacing cables may be bundled together and connect to a RF coil array interfacing cable 920.

The individual coupling electronics units may be housed in a common electronics housing. Each coil loop of the coil array may have respective coupling electronics (e.g., a decoupling circuit, impedance inverter circuit, and pre-amplifier) housed in the housing. In some examples, the common electronics housing may be detachable from the coil loop or RF coil array.

With the RF coil loops not enclosed in the housing, the RF coil array is flexible in multiple dimensions, may not be fixedly connected to one another, and procedures can be performed through the open areas in the coil loops.

Figure 10:
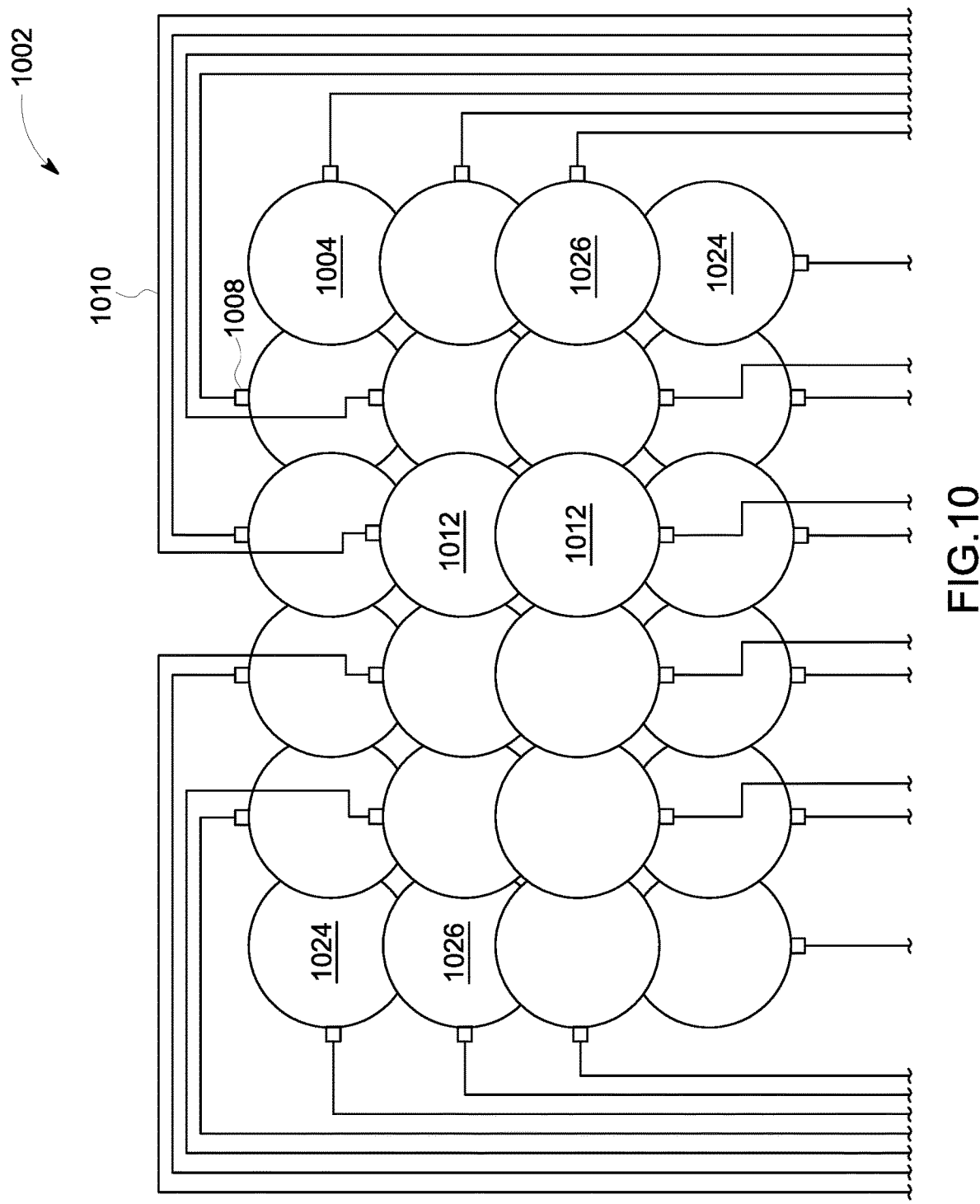
FIG. 10 shows an example RF coil array that may be placed on the body of a subject undergoing an interventional or surgical procedure.

FIG. 10 shows an example RF coil array 1002 that may be placed on the body of a subject undergoing an interventional or surgical procedure. The RF coil array 1002 comprises a middle section 1026 of a plurality of RF coil loops 1004 with associated coupling electronics units 1008 coupled thereto and two outer sections 1024 of a plurality of RF coil loops 1004 with associated coupling electronics units 1008 coupled thereto. The two outer sections 1024 of RF coils are positioned on opposite sides of the middle section 1026 of RF coils. Each of the coupling electronics unit 1008 in the middle section is positioned on the outer periphery of the coil loops and outer perimeter of the middle section. The same is true for the two outer sections 1024 where each coupling electronics unit 1008 in the outer sections is positioned on the outer periphery of the coil loops and outer perimeter of the outer sections. A coil-interfacing cable 1010 extends from each coupling electronics unit 1008. Thus, the coupling electronics units 1008 and coil-interfacing cables 1010 are located away from an open area of RF coils in the middle section 1026 of the RF coil array 1002.

The middle section 1026 of RF coils has no packaging, so the RF coil array has a mostly open area 1012 in the middle section and inside the coil loops providing access to a subject for tissue manipulation or biopsies from interventional or surgical procedures. Also, the RF coils in the middle section 1026 have an optimized SNR because there in minimal interference from electronics and cables.

As mentioned previously, the RF coil array of the present disclosure may be coupled to a RF coil array interfacing cable that includes contiguous, distributed baluns or common-mode traps in order to minimize high currents or standing waves, independent of positioning. High stress areas of the RF coil array interfacing cable may be served by several baluns. Additionally, the thermal load may be shared through a common conductor. The inductance of the central path and return path of the RF coil array interfacing cables are not substantially enhanced by mutual inductance, and therefore are stable with geometry changes. Capacitance is distributed and not substantially varied by geometry changes. Resonator dimensions are ideally very small, but in practice may be limited by blocking requirements, electric and magnetic field intensities, local distortions, thermal and voltage stresses, etc.

Figure 11:
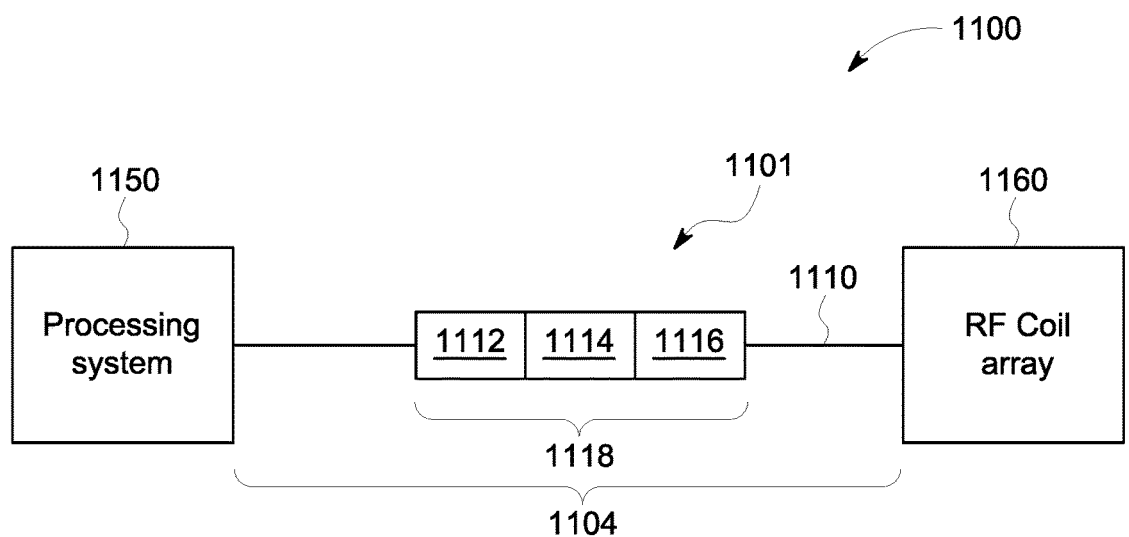
FIG. 11 schematically shows an example RF coil array interfacing cable including a plurality of continuous and/or contiguous common mode traps positioned between a processing system and a RF coil array of a MRI system.

FIG. 11 illustrates a block schematic diagram of a continuous common mode trap assembly 1100 formed in accordance with various embodiments. The common mode trap assembly 1100 may be configured as a transmission cable 1101 configured for transmission of signals between a processing system 1150 and a RF coil array 1160 of an MRI system. Transmission cable 1101 is a non-limiting example of a RF coil array interfacing cable 212 of FIG. 2, processing system 1150 is a non-limiting example of controller unit 210 of FIG. 2, and RF coil array 1160 is a non-limiting example of a plurality of RF coils 202 and coupling electronics 203 of FIG. 2.

In the illustrated embodiment, the transmission cable 1101 (or RF coil array interfacing cable) includes a central conductor 1110 and plural common mode traps 1112, 1114, 1116. It may be noted that, while the common mode traps 1112, 1114, and 1116 are depicted as distinct from the central conductor 1110, in some embodiments, the common mode traps 1112, 1114, 1116 may be integrally formed with or as a part of the central conductor 1110.

The central conductor 1110 in the illustrated embodiment has a length 1104, and is configured to transmit a signal between the RF coil array 1160 and at least one processor of an MRI system (e.g., processing system 1150). The central conductor 1110 may include one or more of a ribbon conductor, a wire conductor, a planar strip conductor, or a coaxial cable conductor, for example. The length 1104 of the depicted central conductor 1110 extends from a first end of the central conductor 1110 (which is coupled to the processing system 1150) to a second end of the central conductor 1110 (which is coupled to the RF coil array 1160). In some embodiments, the central conductor may pass through a central opening of the common mode traps 1112, 1114, 1116.

The depicted common mode traps 1112, 1114, 1116 (which may be understood as cooperating to form a common mode trap unit 1118), as seen in FIG. 11, extend along at least a portion of the length 1104 of the central conductor 1110. In the illustrated embodiment, common mode traps 1112, 1114, 1116 do not extend along the entire length 1104. However, in other embodiments, the common mode traps 1112, 1114, 1116 may extend along the entire length 1104, or substantially along the entire length 1104 (e.g., along the entire length 1104 except for portions at the end configured to couple, for example, to a processor or RF coil array). The common mode traps 1112, 1114, 1116 are disposed contiguously. As seen in FIG. 11, each of the common mode traps 1112, 1114, 1116 is disposed contiguously to at least one other of the common mode traps 1112, 1114, 1116. As used herein, contiguous may be understood as including components or aspects that are immediately next to or in contact with each other. For example, contiguous components may be abutting one another. It may be noted that in practice, small or insubstantial gaps may be between contiguous components in some embodiments. In some embodiments, an insubstantial gap (or conductor length) may be understood as being less than $\frac{1}{40}^{th}$ of a wavelength of a transmit frequency in free space. In some embodiments, an insubstantial gap (or conductor length) may be understood as being two centimeters or less. Contiguous common mode traps, for example, have no (or insubstantial) intervening gaps or conductors therebetween that may be susceptible to induction of current from a magnetic field without mitigation provided by a common mode trap.

For example, as depicted in FIG. 11, the common mode trap 1112 is contiguous to the common mode trap 1114, the common mode trap 1114 is contiguous to the common mode trap 1112 and the common mode trap 1116 (and is interposed between the common mode trap 1112 and the common mode trap 1116), and the common mode trap 1116 is contiguous to the common mode trap 1114. Each of the common mode traps 1112, 1114, 1116 are configured to provide an impedance to the receive transmitter driven currents of an MRI system. The common mode traps 1112, 1114, 1116 in various embodiments provide high common mode impedances. Each common mode trap 1112, 1114, 1116, for example, may include a resonant circuit and/or one or more resonant components to provide a desired impedance at or near a desired frequency or within a target frequency range. It may be noted that the common mode traps 1112, 1114, 1116 and/or common mode trap unit 1118 may also be referred to as chokes or baluns by those skilled in the art.

In contrast to systems having separated discrete common mode traps with spaces therebetween, various embodiments (e.g., the common mode trap assembly 1100) have a portion over which common mode traps extend continuously and/or contiguously, so that there are no locations along the portion for which a common mode trap is not provided. Accordingly, difficulties in selecting or achieving particular placement locations of common mode traps may be reduced or eliminated, as all locations of interest may be included within the continuous and/or contiguous common mode trap. In various embodiments, a continuous trap portion (e.g., common mode trap unit 1118) may extend along a length or portion thereof of a transmission cable. The continuous mode trap portion may be formed of contiguously-joined individual common mode traps or trap sections (e.g., common mode traps 1112, 1114, 1116). Further, contiguous common mode traps may be employed in various embodiments to at least one of lower the interaction with coil elements, distribute heat over a larger area (e.g., to prevent hot spots), or help ensure that blocking is located at desired or required positions. Further, contiguous common mode traps may be employed in various embodiments to help distribute voltage over a larger area. Additionally, continuous and/or contiguous common mode traps in various embodiments provide flexibility. For example, in some embodiments, common mode traps may be formed using a continuous length of conductor(s) (e.g., outer conductors wrapped about a central conductor) or otherwise organized as integrally formed contiguous sections. In various embodiments, the use of contiguous and/or continuous common mode traps (e.g., formed in a cylinder) provide for a range of flexibility over which flexing of the assembly does not substantially change the resonant frequency of the structure, or over which the assembly remains on frequency as it is flexed.

It may be noted that the individual common mode traps or sections (e.g., common mode traps 1112, 1114, 1116) in various embodiments may be constructed or formed generally similarly to each other (e.g., each trap may be a section of a length of tapered wound coils), but each individual trap or section may be configured slightly differently than other traps or sections. For example, in some embodiments, each common mode trap 1112, 1114, 1116 is tuned independently. Accordingly, each common mode trap 1112, 1114, 1116 may have a resonant frequency that differs from other common mode traps of the same common mode trap assembly 1100.

Alternatively or additionally, each common mode trap may be tuned to have a resonant frequency near an operating frequency of the MRI system. As used herein, a common mode trap may be understood as having a resonant frequency near an operating frequency when the resonant frequency defines or corresponds to a band that includes the operating frequency, or when the resonant frequency is close enough to the operating frequency to provide on-frequency blocking, or to provide a blocking impedance at the operating frequency.

Further additionally or alternatively, each common mode trap may be tuned to have a resonant frequency below an operating frequency of the MRI system (or each common mode trap may be tuned to have resonant frequency above an operating frequency of the MRI system). With each trap having a frequency below (or alternatively, with each trap having a frequency above) the operating frequency, the risk of any of the traps canceling each other out (e.g., due to one trap having a frequency above the operating frequency and a different trap having a frequency below the operating frequency) may be eliminated or reduced. As another example, each common mode trap may be tuned to a particular band to provide a broadband common mode trap assembly.

In various embodiments, the common mode traps may have a two-dimensional (2D) or three-dimensional (3D) butterfly configuration to counteract magnetic field coupling and/or local distortions.

Figure 12:
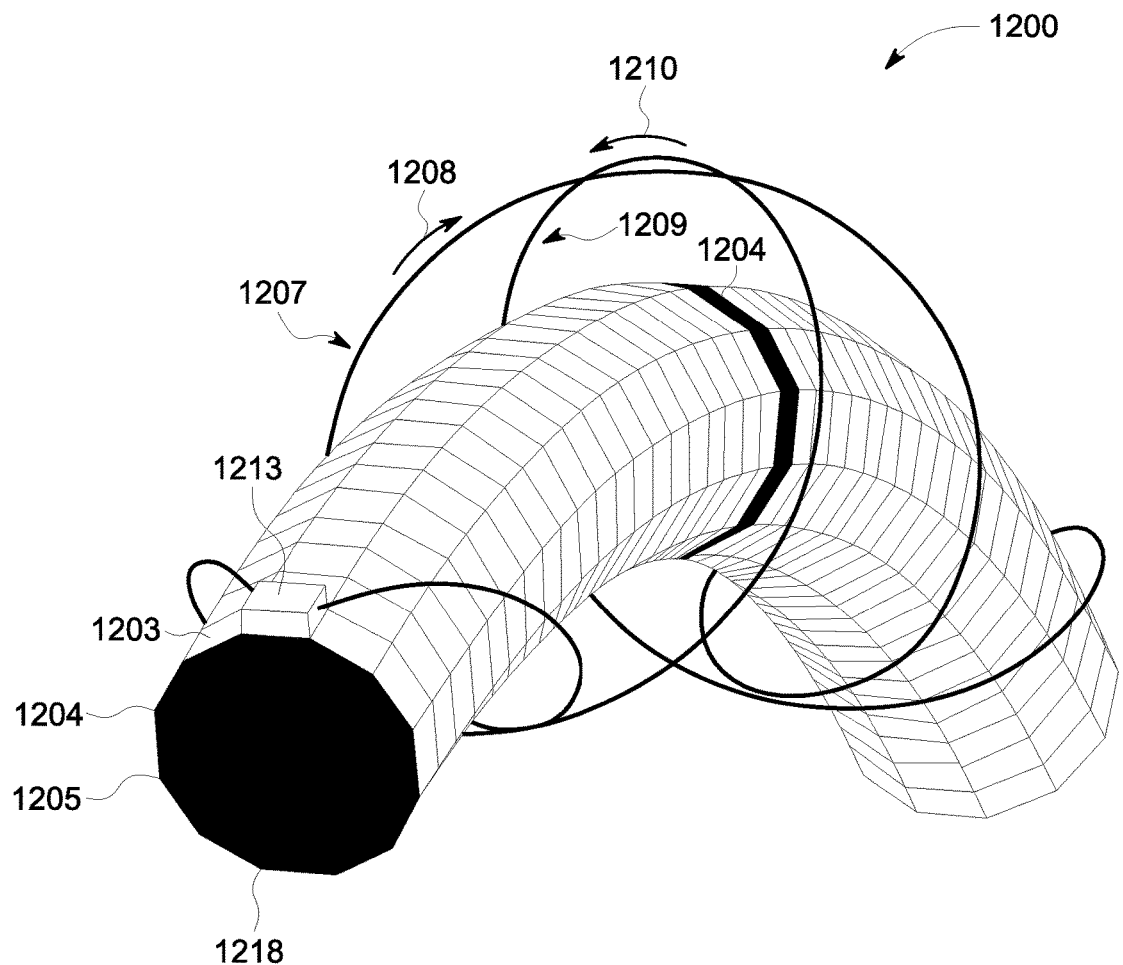
FIGS. 12 and 13 schematically show example RF coil array interfacing cables including a plurality of continuous and/or contiguous common mode traps.

FIG. 12 is a perspective view of a RF coil array interfacing cable 1200 including a plurality of continuous and/or contiguous common mode traps according to an embodiment of the disclosure. The RF coil array interfacing cable 1200 includes an outer sleeve or shield 1203, a dielectric spacer 1204, an inner sleeve 1205, a first common mode trap conductor 1207, and a second common mode trap conductor 1209.

The first common mode trap conductor 1207 is wrapped in a spiral about the dielectric spacer 1204, or wrapped in a spiral at a tapering distance from a central conductor (not shown) disposed within the bore 1218 of the RF coil array interfacing cable 1200, in a first direction 1208. Further, the second common mode trap conductor 1209 is wrapped in a spiral about the dielectric spacer 1204, or wrapped in a spiral at a tapering distance from the central conductor disposed within the bore 1218, in a second direction 1210 that is opposite to the first direction 1208. In the illustrated embodiment, the first direction 1208 is clockwise and the second direction 1210 is counter-clockwise.

The conductors 1207 and 1209 of the RF coil array interfacing cable 1200 may comprise electrically-conductive material (e.g., metal) and may be shaped as ribbons, wires, and/or cables, for example. In some embodiments, the counterwound or outer conductors 1207 and 1209 may serve as a return path for a current passing through the central conductor. Further, in various embodiments, the counterwound conductors 1207 and 1209 may cross each other orthogonally (e.g., a center line or path defined by the first common mode trap conductor 1207 is perpendicular to a center line or path defined by the second common mode trap conductor 1209 as the common mode trap conductors cross paths) to eliminate, minimize, or reduce coupling between the common mode trap conductors.

It may be further noted that in various embodiments the first common mode trap conductor 1207 and the second common mode trap conductor 1209 are loosely wrapped about the dielectric spacer 1204 to provide flexibility and/or to reduce any binding, coupling, or variation in inductance when the RF coil array interfacing cable 1200 is bent or flexed. It may be noted that the looseness or tightness of the counterwound outer conductors may vary by application (e.g., based on the relative sizes of the conductors and dielectric spacer, the amount of bending or flexing that is desired for the common mode trap, or the like). Generally, the outer or counterwound conductors should be tight enough so that they remain in the same general orientation about the dielectric spacer 1204, but loose enough to allow a sufficient amount of slack or movement during bending or flexing of the RF coil array interfacing cable 1200 to avoid, minimize, or reduce coupling or binding of the counterwound outer conductors.

In the illustrated embodiment, the outer shielding 1203 is discontinuous in the middle of the RF coil array interfacing cable 1200 to expose a portion of the dielectric spacer 1204 which in some embodiments is provided along the entire length of the RF coil array interfacing cable 1200. The dielectric spacer 1204, may be comprised, as a non-limiting example, of TEFLON® or another dielectric material. The dielectric spacer 1204 functions as a capacitor and thus may be tuned or configured to provide a desired resonance. It should be appreciated that other configurations for providing capacitance to the RF coil array interfacing cable 1200 are possible, and that the illustrated configurations are exemplary and non-limiting. For example, discrete capacitors may alternatively be provided to the RF coil array interfacing cable 1200.

Further, the RF coil array interfacing cable 1200 includes a first post 1213 and a second post (not shown) to which the first common mode trap conductor 1207 and the second common mode trap conductor 1209 are fixed. To that end, the first post 1213 and the second post are positioned at the opposite ends of the common mode trap, and are fixed to the outer shielding 1203. The first post 1213 and the second post ensure that the first and second common mode trap conductors 1207 and 1209 are positioned close to the outer shielding 1203 at the ends of the RF coil array interfacing cable 1200, thereby providing a tapered butterfly configuration of the counterwound conductors as described further herein.

The tapered butterfly configuration includes a first loop formed by the first common mode trap conductor 1207 and a second loop formed by the second common mode trap conductor 1209, arranged so that an induced current (a current induced due to a magnetic field) in the first loop and an induced current in the second loop cancel each other out. For example, if the field is uniform and the first loop and the second loop have equal areas, the resulting net current will be zero. The tapered cylindrical arrangement of the loops provide improved flexibility and consistency of resonant frequency during flexing relative to two-dimensional arrangements conventionally used in common mode traps.

Generally, a tapered butterfly configuration as used herein may be used to refer to a conductor configuration that is flux cancelling, for example including at least two similarly sized opposed loops that are symmetrically disposed about at least one axis and are arranged such that currents induced in each loop (or group of loops) by a magnetic field tends to cancel out currents induced in at least one other loop (or group of loops). For example, with reference to FIG. 11, in some embodiments, counterwound conductors (e.g., conductors wound about a central member and/or axis in opposing spiral directions) may be spaced a distance radially from the central conductor 1110 to form the common mode traps 1112, 1114, 1116. As depicted in FIG. 12, the radial distance may be tapered towards the end of the common mode traps to reduce or altogether eliminate fringe effects. In this way, the common mode traps 1112, 1114, 1116 may be continuously or contiguously positioned without substantial gaps therebetween.

Figure 13:
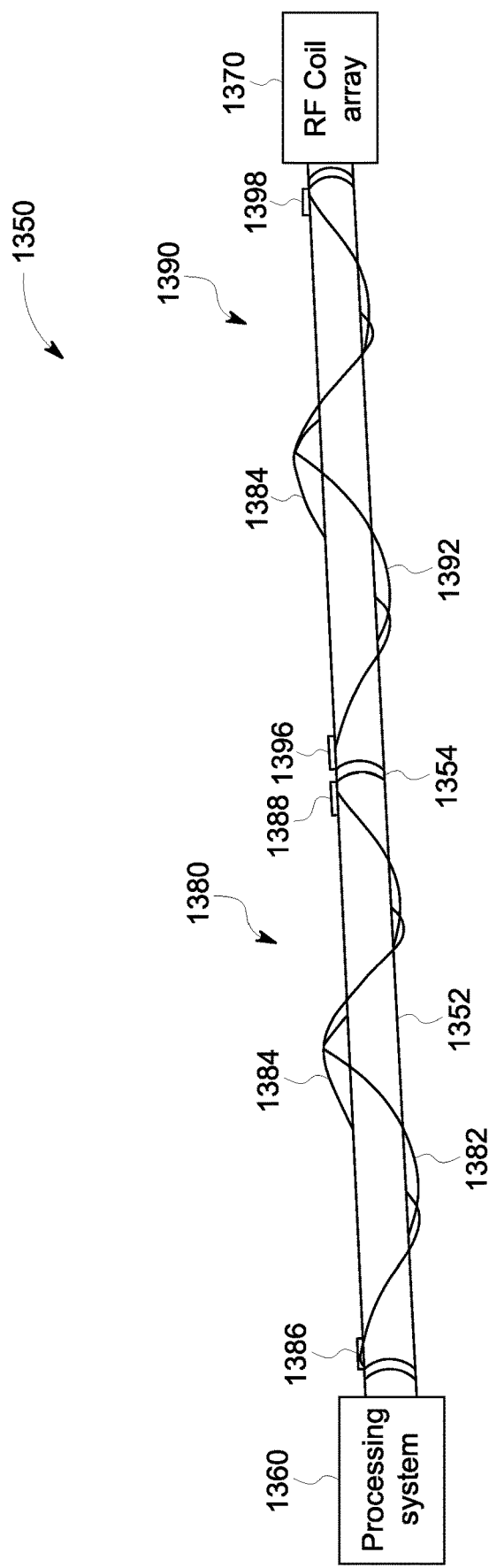

The tapered spiral configuration of the common mode trap conductors described herein above is particularly advantageous when multiple common mode trap conductors are contiguously disposed in a common mode trap assembly. As an illustrative example, FIG. 13 is a perspective view of a RF coil array interfacing cable 1350 including a plurality of continuous and/or contiguous common mode traps coupling an RF coil array 1370 to a processing system 1360. RF coil array interfacing cable 1350 includes a first common mode trap 1380 and a second common mode trap 1390 positioned adjacent to each other on a central conductor 1352.

The first common mode trap 1280 includes a first common mode trap conductor 1382 and a second common mode trap conductor 1384 counterwound in a tapered spiral configuration. To that end, the first and second conductors 1382 and 1384 are fixed to posts 1386 and 1388. It should be noted that the posts 1386 and 1388 are aligned on a same side of the common mode trap 1380.

Similarly, the second common mode trap 1390 includes a third common mode trap conductor 1392 and a fourth common mode trap conductor 1394 counterwound in a tapered spiral configuration and fixed to posts 1396 and 1398. It should be noted that the posts 1396 and 1398 are aligned on a same side of the common mode trap 1390.

As depicted, the common mode traps 1380 and 1390 are separated by a distance, thereby exposing the central conductor 1352 in the gap 1354 between the common mode traps. Due to the tapering spiral configuration of the common mode trap conductors of the common mode traps, the gap 1354 can be minimized or altogether eliminated in order to increase the density of common mode traps in a common mode trap assembly without loss of impedance functions of the common mode traps. That is, the distance can be made arbitrarily small such that the common mode traps are in face-sharing contact, given the tapered spiral configuration.

It should be appreciated that while the RF coil array interfacing cable 1350 includes two common mode traps 1380 and 1390, in practice a RF coil array interfacing cable may include more than two common mode traps.

Further, the common mode traps 1380 and 1390 of the RF coil array interfacing cable 1350 are aligned such that the posts 1386, 1388, 1396, and 1398 are aligned on a same side of the RF coil array interfacing cable. However, in examples where cross-talk between the common mode traps may be possible, for example if the tapering of the counterwound conductors is more severe or steep, the common mode traps may be rotated with respect to one another to further reduce fringe effects and/or cross-talk between the traps.

Additionally, other common mode trap or balun configurations are possible. For example, the exterior shielding of each common mode trap may be trimmed such that the common mode traps can be overlapped or interleaved, thus increasing the density of the common mode traps.

As used herein, an element or step recited in the singular and proceeded with the word "a" or "an" should be understood as not excluding plural of said elements or steps, unless such exclusion is explicitly stated. Furthermore, references to "one embodiment" of the present disclosure are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A radio frequency (RF) coil array assembly for a magnetic resonance imaging (MRI) system, comprising:
   a plurality of RF coils, each RF coil comprising two distributed capacitance wire conductors shaped into a loop portion, wherein the two distributed capacitance wire conductors are encapsulated and separated by a dielectric material, and the loop portion is void of discrete capacitive components and discrete inductive components; and
   at least one coupler slidably connecting the loop portions of two adjacent RF coils,
   wherein the loop portions of two adjacent RF coils are movable relative to each other via the two distributed capacitance wire conductors sliding through the at least one coupler, and an open area is formed inside the loop portion of each RF coil to provide interventional access through the loop portion to an anatomy of a subject to be imaged.

2. The RF coil array assembly of claim 1, wherein each RF coil further comprises a coupling electronics portion that includes a decoupling circuit configured to decouple the RF coil during a transmit operation and an impedance inverter circuit.

3. The RF coil array assembly of claim 2, wherein the coupling electronics portion of each RF coil further includes a pre-amplifier with low impedance.

4. The RF coil array assembly of claim 2, wherein each RF coil further comprises a coil-interfacing cable extending between the coupling electronics portion and an interfacing connector of the RF coil array assembly.

5. The RF coil array assembly of claim 1, wherein a shape of each RF coil is variable according to the anatomy of the subject.

6. The RF coil array assembly of claim 1, wherein a groove is formed on the at least one coupler to slidably engage the loop portions of two adjacent RF coils.

7. A method comprising:
   attaching a radio frequency (RF) coil array assembly to an anatomy of a subject for receiving magnetic resonance (MR) signals from the anatomy, wherein the RF coil array comprises a plurality of RF coils, wherein each RF coil comprises two distributed capacitance wire conductors shaped into a loop portion, wherein the two distributed capacitance wire conductors are encapsulated and separated by a dielectric material, and the loop portion is void of discrete capacitive components and discrete inductive components; and
   accessing the anatomy of the subject through at least one open area formed inside the loop portion of each RF coil of the RF coil array assembly.

8. The method of claim 7, wherein the anatomy is a head.

9. The method of claim 7, wherein the RF coil array assembly further comprises at least one coupler slidably connecting the loop portions of two adjacent RF coils, and the loop portions of two adjacent RF coils are movable relative to each other via the two distributed capacitance wire conductors sliding through the at least one coupler.

10. The method of claim 9, wherein a groove is formed on the at least one coupler to slidably engage the loop portions of two adjacent RF coils.

11. The method of claim 7, wherein each RF coil further comprises a coupling electronics portion that includes a decoupling circuit configured to decouple the RF coil during a transmit operation and an impedance inverter circuit.

12. The method of claim 11, wherein the coupling electronics portion of each RF coil further includes a pre-amplifier with low impedance.

13. The method of claim 7, further comprising:
   performing an interventional or surgical procedure on the anatomy through the at least one open area.

14. The method of claim 13, further comprising:
   using the MR signals received by the RF coil array assembly to guide the interventional or surgical procedure.

15. The RF coil array assembly of claim 1, wherein the two distributed capacitance wire conductors are stranded wire.

16. The RF coil array assembly of claim 1, wherein the loop portion conforms to the anatomy of the subject.

17. The RF coil array assembly of claim 1, wherein the two distributed capacitance wire conductors are parallel to each other.

18. The RF coil array assembly of claim 1, wherein each RF coil does not include packaging around the RF coil.

19. The RF coil array assembly of claim 4, wherein the coil-interfacing cable comprises one or more distributed baluns.

20. A radio frequency (RF) coil array assembly for a magnetic resonance imaging (MRI) system, comprising:
   a plurality of RF coils, each RF coil comprising two distributed capacitance wire conductors shaped into a loop portion, wherein the two distributed capacitance wire conductors are encapsulated and separated by a dielectric material, and the loop portion is void of discrete capacitive components and discrete inductive components; and
   at least one coupler slidably connecting the loop portions of two adjacent RF coils,
   wherein an open area is formed inside the loop portion of each RF coil to provide interventional access to an anatomy of a subject to be imaged.

* * * * *